United States Patent
Sheng et al.

(10) Patent No.: US 10,549,116 B2
(45) Date of Patent: Feb. 4, 2020

(54) RADIOTHERAPY UTILIZING THE ENTIRE 4PI SOLID ANGLE

(71) Applicant: The Regents of the University of California, Oakland, CA (US)

(72) Inventors: Ke Sheng, Los Angeles, CA (US); Dan Ruan, Los Angeles, CA (US); Daniel A. Low, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 314 days.

(21) Appl. No.: 15/555,669

(22) PCT Filed: Mar. 1, 2016

(86) PCT No.: PCT/US2016/020234
§ 371 (c)(1),
(2) Date: Sep. 5, 2017

(87) PCT Pub. No.: WO2016/140955
PCT Pub. Date: Sep. 9, 2016

(65) Prior Publication Data
US 2018/0043183 A1  Feb. 15, 2018

Related U.S. Application Data

(60) Provisional application No. 62/128,906, filed on Mar. 5, 2015.

(51) Int. Cl.
*A61N 5/00* (2006.01)
*A61N 5/10* (2006.01)

(52) U.S. Cl.
CPC .......... *A61N 5/103* (2013.01); *A61N 5/1047* (2013.01); *A61N 5/1082* (2013.01);
(Continued)

(58) Field of Classification Search
CPC .... A61N 5/103; A61N 5/1037; A61N 5/1047; A61N 5/1082
(Continued)

(56) References Cited

U.S. PATENT DOCUMENTS

| 3,720,817 | A | 3/1973 | Dinwiddie |
| 6,651,279 | B1 | 11/2003 | Muthuvelan |

(Continued)

FOREIGN PATENT DOCUMENTS

| WO | 2014018983 A1 | 1/2014 |
| WO | 2015017639 A1 | 2/2015 |

OTHER PUBLICATIONS

European Patent Office, Extended European Search Report, Application No. 16759347.4, dated Nov. 23, 2018, 7 pages.
(Continued)

*Primary Examiner* — John P Lacyk
(74) *Attorney, Agent, or Firm* — Quarles & Brady LLP

(57) ABSTRACT

In various embodiments, methods and devices are provided for generating a radiotherapy treatment plan for a subject to be implemented on a radiotherapy device. In certain embodiments the methods involve determining all feasible radiotherapy beam orientations free of collision for said radiotherapy device and said subject to provide a set of radiotherapy beam orientations; selecting from the set of all feasible radiotherapy beam orientations a subset of beams that meet treatment goals to be used in treatment of the subject to provide a selected beam set; calculating a navigation trajectory for the radiotherapy device to delivery said subset of beams to the subject where the trajectory is free of collision; and generating and writing instruction files to a tangible medium that can be executed by said radiotherapy device.

27 Claims, 13 Drawing Sheets

(52) U.S. Cl.
CPC ...... *A61N 2005/109* (2013.01); *A61N 2005/1087* (2013.01); *A61N 2005/1089* (2013.01)

(58) Field of Classification Search
USPC .......................................................... 600/1
See application file for complete search history.

(56) References Cited

U.S. PATENT DOCUMENTS

| | | |
|---|---|---|
| 7,046,765 B2 | 5/2006 | Wong et al. |
| 7,103,144 B2 | 9/2006 | Wong et al. |
| 7,103,145 B2 | 9/2006 | Wong et al. |
| 7,130,372 B2 | 10/2006 | Cusch et al. |
| 7,280,633 B2 | 10/2007 | Cheng et al. |
| 7,746,978 B2 | 6/2010 | Cheng et al. |
| 7,949,096 B2 | 5/2011 | Cheng et al. |
| 8,569,720 B2 | 10/2013 | Rigney et al. |
| 8,750,453 B2 | 6/2014 | Cheng et al. |
| 8,855,812 B2 | 10/2014 | Kapoor |
| 9,486,647 B2 | 11/2016 | Bergfjord et al. |
| 9,623,263 B2 | 4/2017 | Cheng et al. |
| 10,272,265 B2 | 4/2019 | Filiberti |
| 2010/0303205 A1 | 12/2010 | Kapoor et al. |
| 2010/0320402 A1 | 12/2010 | Wu et al. |
| 2011/0249088 A1 | 10/2011 | Hannibal et al. |
| 2012/0020460 A1 | 1/2012 | Witten et al. |
| 2012/0136194 A1 | 5/2012 | Zhang et al. |
| 2013/0142310 A1 | 6/2013 | Fahimian et al. |
| 2015/0032233 A1 | 1/2015 | Cheng et al. |
| 2015/0035942 A1 | 2/2015 | Hampton et al. |
| 2016/0073978 A1 | 3/2016 | Henderson et al. |
| 2016/0161938 A1 | 6/2016 | Popple et al. |
| 2016/0166856 A1 | 6/2016 | Popple et al. |
| 2017/0087389 A1 | 3/2017 | Benner et al. |
| 2017/0220709 A1 | 8/2017 | Wan et al. |

OTHER PUBLICATIONS

Becker (2011) J. Appl. Clin. Med. Phys. 12: 3405.
Chao et al. (2001) J. Digit. Imaging, 14: 186-191.
Hamza-Lup et al. (2008) Int. J. Comput. Assist. Radiol. Surg. 3: 275-281.
Hua et al. (2004) Med. Phys. 31: 2128-2134.
Humm (1994) Med. Phys. 21: 1053-1064.
Humm et al. (1995) Int. J. Radiat. Oncol. Biol. Phys. 33: 1101-1108.
Nioutsikou et al. (2003) Phys. Med. Biol. 48: N313-N321.
Thieke et al. (2002) Acta Oncologica 41:158-161.
Tsiakalos et al. (2001) Med. Phys. 28: 1359-1363.
PCT International Search Report and Written Opinion, PCT/US2016/020234, dated Jun. 14, 2016, 13 pages.
Padilla et al. "Collision prediction software for radiotherapy treatments." Med. Phys. vol. 42(11): 6448-56, Nov. 2015.
Zou et al. "A clinically feasible method for the detection of potential collision in proton therapy," Med. Phys. vol. 39(11): 7094-101, Nov. 2012.
Hamza-Lup FG et al. "X3D in radiation Therapy Procedure Planning," International Conference on Web Information System and Technologies, Jan. 2007.
Beange et al. "A collision prevention software tool for complex three-dimensional isocentric set-ups," Brit. J. of Rad. Vo. 73:537-541, 2000.

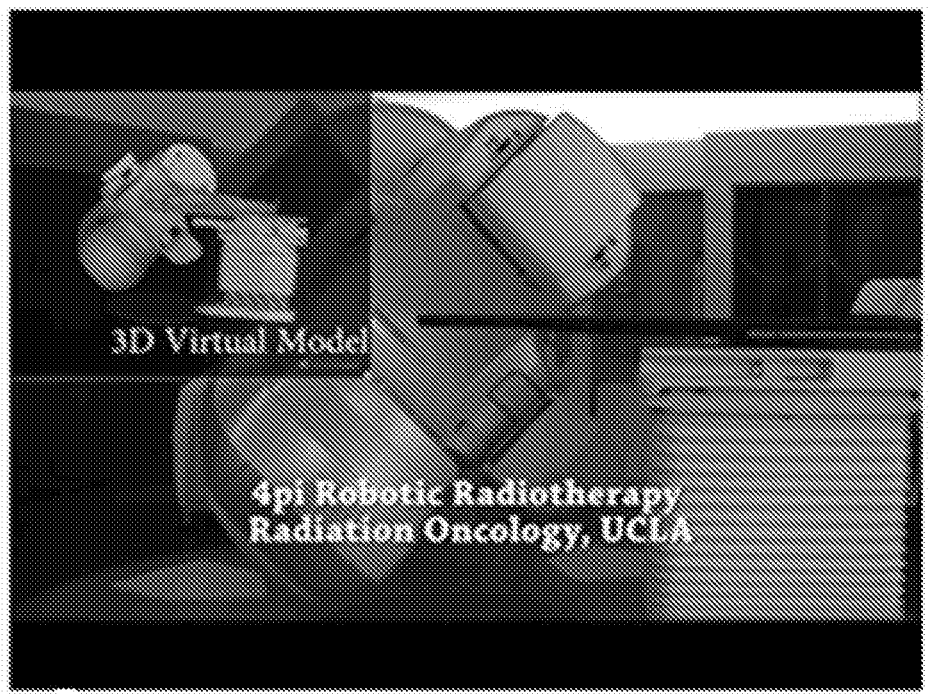
C
*Fig. 5, cont'd.*

C
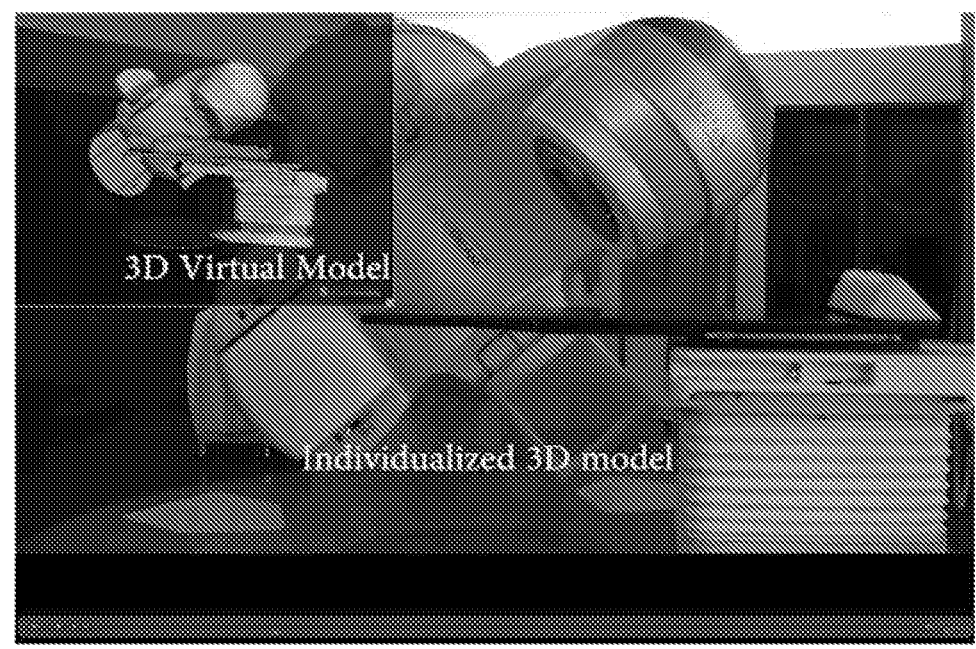
D
*Fig. 6, cont'd.*

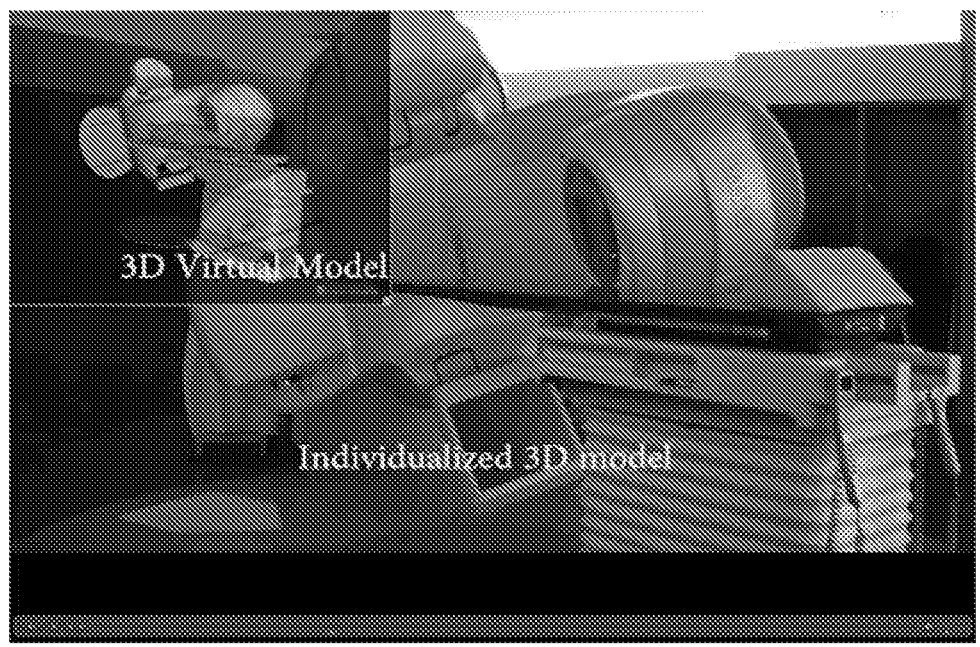
E
F
*Fig. 6, cont'd.*

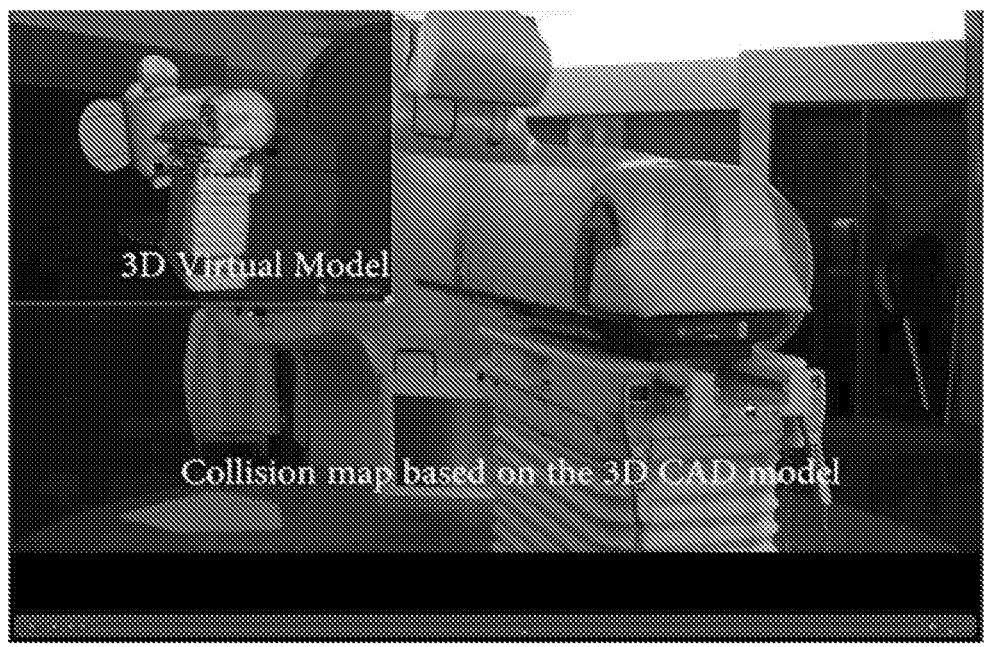
G
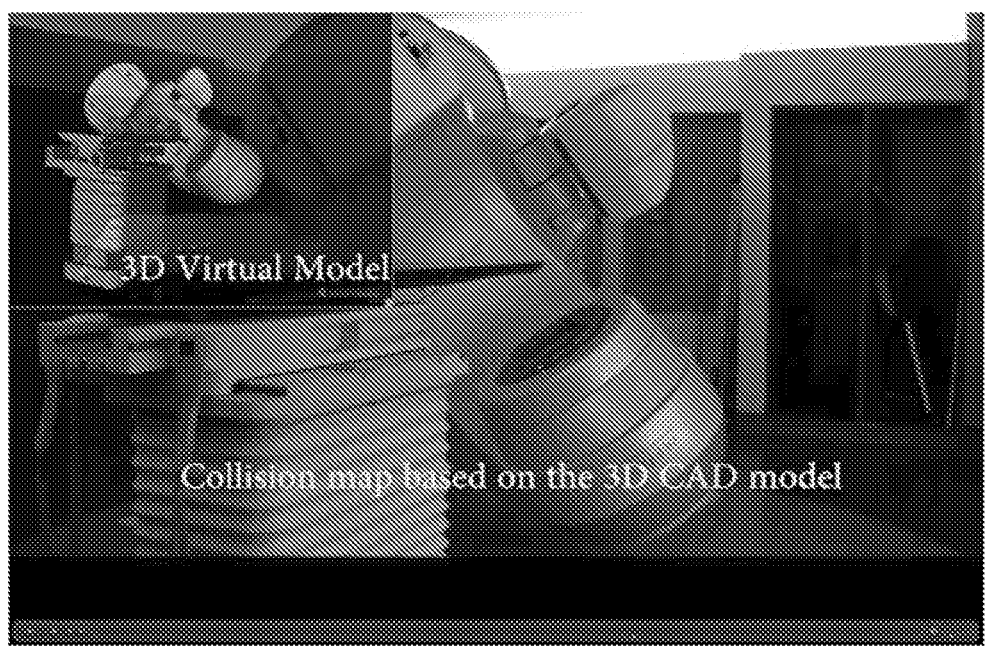
H
*Fig. 6, cont'd.*

RADIOTHERAPY UTILIZING THE ENTIRE 4PI SOLID ANGLE

CROSS-REFERENCE TO RELATED APPLICATIONS

This application represents the national stage entry of PCT International Application PCT/US2016/020234 filed Mar. 1, 2016 and claims priority to U.S. Provisional Patent Application 62/128,906 filed Mar. 5, 2015. The contents of this application are hereby incorporated by reference as if set forth in their entirety herein.

STATEMENT OF GOVERNMENTAL SUPPORT

[Not Applicable]

BACKGROUND

Radiation treatment or radiotherapy involves the treatment of a disease with radiation, typically by selective irradiation with x-rays or other ionizing radiation and/or by ingestion or surgical implantation of radioisotopes. During radiation treatment, for example, high-energy x-rays or electron beams are generated, e.g., by a linear accelerator (LINAC) and directed towards a target (e.g. a tumor). The goal of the treatment is to destroy the cancerous cells within the target without causing undue side effects that may result from harming surrounding healthy tissue and vital organs during treatment.

To treat regions within the body of the subject, however, the radiation must typically penetrate healthy tissue in order to irradiate the internal treatment volume and destroy pathological cells therein. In conventional radiation therapy, large volumes of healthy tissue can thus be exposed to harmful doses of radiation, resulting in prolonged recovery periods for the patient. Radiotherapy treatment plans are often constructed to achieve the desired on-site exposure whilst keeping the exposure of healthy cells to a minimum.

Many methods work by directing radiation at a tumor from a number of directions, either simultaneously from multiple sources or multiple exposures from a single source. The intensity of radiation emanating from each source is therefore less than would be required to destroy cells, but where the radiation beams from the multiple sources converge, the intensity of radiation is sufficient to deliver a therapeutic dose.

The point of intersection of the multiple radiation beams is herein referred to as the "target point". The radiation field surrounding a target point is herein referred to as the "target volume", the size of which can be varied by varying the size of the intersecting beams.

Radiation treatment typically takes place over one or a course of several sessions during which a delivered radiation dose is broken into a plurality of portal fields. For each field, a LINAC gantry is rotated to different angular positions, spreading out the dose delivered to healthy tissue. At the same time, the beam remains pointed towards the target anatomy, which may be placed in the isocenter of the beam by positioning the patient.

Such radiation therapy is rationally delivered with the radiation source revolving around the patient superior/inferior axis. The source trajectory is referred to as coplanar geometry. Coplanar source trajectories are simpler to plan and deliver.

Although adding beams from non-coplanar trajectories can improve the dosimetry and reduce normal organ doses from radiotherapy, such treatment methods are not easily achievable due to the difficulties in plan optimization, collision avoidance and the creation of an efficient beam path so that a non-coplanar plan can be delivered within the time allowed by clinical work flow.

SUMMARY

In various embodiments a sophisticated system to address technical difficulties associated with non-coplanar treatment so the radiation dosimetry can be significantly, safely and efficiently improved is provided herein.

Various embodiments contemplated herein may include, but need not be limited to, one or more of the following

Embodiment 1

A method of generating a radiotherapy treatment plan for a subject to be implemented on a radiotherapy device, said method including: determining all feasible radiotherapy beam orientations free of collision for said radiotherapy device and said subject to provide a set of radiotherapy beam orientations; selecting from said set of all feasible radiotherapy beam orientations a subset of beams that meet treatment goals to be used in treatment of said subject to provide a selected beam set; calculating a navigation trajectory for said radiotherapy device to delivery said subset of beams to said subject where said trajectory is free of collision; and generating and writing instruction files to a tangible medium that can be executed by said radiotherapy device.

Embodiment 2

The method of embodiment 1, wherein said calculating a trajectory includes calculating a trajectory that minimizes treatment delivery time.

Embodiment 3

The method according to any one of embodiments 1-2, wherein said determining includes: providing a map of the three-dimensional surface of said subject as positioned on a radiotherapy treatment couch to generate a three-dimensional patient surface model; and constructing a virtual treatment room by fusing the patient surface model onto a model of the treatment machine.

Embodiment 4

The method of embodiment 3, wherein said providing a map includes performing a 3 dimensional scan of said subject using a 3 dimensional scanner.

Embodiment 5

The method of embodiment 4, wherein said 3 dimensional scanner is a non-contact active scanner.

Embodiment 6

The method according to any one of embodiments 4-5, wherein said scanner is a time of flight active scanner.

Embodiment 7

The method according to any one of embodiments 4-5, wherein said scanner is a triangulation based 3D laser scanner.

Embodiment 8

The method according to any one of embodiments 4-5, wherein said scanner is a structured light 3D scanner.

Embodiment 9

The method according to any one of embodiments 4-8, wherein a plurality of 3D scanner cameras are mounted in a room above a subject couch.

Embodiment 10

The method of embodiment 9, wherein said cameras provide a combined view of the patient anterior and lateral surfaces.

Embodiment 11

The method according to any one of embodiments 9-10, wherein said is longitudinally translated during the optical scanning procedure, providing a 3D optical substantially equivalent to a topogram.

Embodiment 12

The method according to any one of embodiments 4-11, wherein the 3D measurement accuracy is better than about 5 mm, or better than about 4 mm, or better than about 3 mm, or better than about 2 mm, or better than about 1 mm.

Embodiment 13

The method according to any one of embodiments 4-12, where the scan time is less than about 10 minutes, or less than about 5 minutes, or less than about 4 minutes, or less than about 3 minutes, or less than about 2 minutes, or less than about 1 minute, or less than about 30 seconds.

Embodiment 14

The method according to any one of embodiments 1-13, wherein said selecting a subset of beams beam angles consistent with an isocentric geometry.

Embodiment 15

The method of embodiment 14, wherein said selecting is for treatment of sites in the cranium, and/or upper head, and/or neck.

Embodiment 16

The method according to any one of embodiments 1-13, wherein said selecting a subset of beams beam angles consistent with a non-isocentric geometry.

Embodiment 17

The method according to any one of embodiments 14-16, wherein beam angles that cannot be utilized because the couch cannot be moved far enough to get out of the way of the gantry, or the gantry would collide with the pedestal, are excluded from the VRS.

Embodiment 18

The method according to any one of embodiments 14-17, wherein said selecting utilizes a Direct Aperture Optimization (DAO) algorithm for intensity modulation and leaf sequencing.

Embodiment 19

The method of embodiments 18, wherein said method combines fluence map optimization and leaf sequencing into a single step.

Embodiment 20

The method according to any one of embodiments 18-19, wherein when $D_{bk}$ denotes the dose delivered to a volume from aperture $a \in K_b$ in beam $b \in B$ and $F(z)$ the objective function associated with dose distribution z, beam selectin optimization is formulated as:

$$\text{minimize } F(\vec{z}) \qquad (1)$$

$$\text{s.t.} \begin{cases} \vec{z} = \sum_{b \in B} \sum_{k \in K_b} D_{bk} x_{bk}, x_{bk,} \geq 0, k \in K', b \in B \\ x_{bk} = 0, b \in B \setminus B', k \in K' \\ \vec{z} \leq \vec{q} \end{cases}$$

where $K_b$ is the set of deliverable apertures at angle b, B' represents selected beam orientation sets, $\vec{z}$ is the 3D dose distribution, $\vec{q}$ is the 3D dose constraint.

Embodiment 21

The method of embodiment 20, wherein a column generation algorithm is used to determine the contents of B' while explicitly taking into account the treatment plan quality.

Embodiment 22

The method according to any one of embodiments 20-21, wherein optimization starts from an empty solution set and for each iteration, beams from the remainder of a candidate beam pool B\B' are individually added to the selected beam set, and the direct aperture optimization problem is subsequently solved; the beam that contributes most to the plan optimization objective function is kept and all other beams are returned to the candidate beam pool; and the iterative process continues until the desired number of beams is reached or the objective function plateaued.

Embodiment 23

The method according to any one of embodiments 20-22, wherein, the instantaneous change in the objective value of the optimal solution per unit of the constraint of solving the direct aperture optimization model with selected B' beams is used to predict the value of a new beam.

Embodiment 24

The method according to any one of embodiments 20-22, wherein the objective function F(z) is defined based on a linear approximation of equivalent uniform dose (EUD):

$$\begin{cases} F(\vec{z}) = \sum_m \alpha_m G_m(\vec{z}) \, m \in r, s, r_{50}, V_{d_1 Gy}, V_{d_2 Gy}, \ldots V_{d_n Gy}, \alpha_m \geq 0 & (2) \\ Gr(\vec{z}) = \text{mean}(\max(\text{prescription dose} - \vec{z}, 0)) \cdot \text{ for } PTV\ r \\ Gs(\vec{z}) = h_s \, \text{mean}(\vec{z}) + (1 - h_s)\max(\vec{z}) \text{ for } OARs\ h_s \leq 1 \\ Gr_{50}(\vec{z}) = h_{r_{50}}\text{mean}(\max(\vec{z} - 0.5 * \text{prescription dose}, 0)) \\ \qquad \text{for ring structures} \\ G_{V_{d_1 Gy}}(\vec{z}) = \text{mean}(\max(\vec{z} - d_1, 0)) \\ \qquad \text{for an } OAR \text{ such as the lung or heart} \\ G_{V_{d_2 Gy}}(\vec{z}) = \text{mean}(\max(\vec{z} - d_2, 0)) \\ \qquad \ldots \\ G_{V_{d_n Gy}}(\vec{z}) = \text{mean}(\max(\vec{z} - d_n, 0)) \end{cases}$$

where $G_s$, $G_r$, $G_{r_{50}}$, $G_{V_{d_1 Gy}}$, $G_{V_{d_2 Gy}}$ and $G_{V_{d_3 Gy}}$ are objective functions for organs-at-risks (OARs), PTVs, dose gradient as defined by the ratio between the 50% isodose volume and PTV, and the volume of a specific organ receiving greater than $d_1, d_2, \ldots d_n$ doses. $h_s$ is used to adjust the relative weighting of average and maximum dose for serial or parallel organs. $\alpha_m \geq 0$ for OARs, $\alpha_m \leq 0$ for PTV, $h_s \leq 1$, $h_r \leq 1$, respectively.

Embodiment 25

The method of embodiment 24, wherein the weights among multi objectives $\alpha_m$'s are fine-tuned to reach individual planning objectives.

Embodiment 26

The method according to any one of embodiments 24-25, wherein a shell-shaped structure is added as isotropic expansion of PTV to apply a dose gradient constraint.

Embodiment 27

The method according to any one of embodiments 24-26, wherein assignment of a voxel that that lies within multiple organs at risk (OARs) is given to the OAR with greatest optimization priority, which is manually determined.

Embodiment 28

The method according to any one of embodiments 24-27, wherein the number of beams is determined based on the incremental gains in dose conformality ($R_{50}$), which decreases as the number of optimized non-coplanar angles increases.

Embodiment 29

The method of embodiment 28, wherein a minimal number of beams is used to reach the optimization goal.

Embodiment 30

The method of embodiment 28, wherein the optimization goal is reached with less than about 50 beams, or less than about 40 beams, or less than about 30 beams.

Embodiment 31

The method according to any one of embodiments 20-30, wherein the initial set of apertures per beam is limited as denoted by $\hat{K}_b \in K_b$ and at each iteration, a restricted version of Equation (1) is solved using only the apertures within $\hat{K}_b$.

Embodiment 32

The method of embodiment 31, wherein an optimization subproblem is solved that either (i) identifies one or more promising apertures that improve the current solution when added to $\hat{K}$; or (ii) concludes that no such aperture exists and therefore the current solution is optimal.

Embodiment 33

The method according to any one of embodiments 1-32, wherein said calculating a navigation trajectory provides continuous explicit collision avoidance.

Embodiment 34

The method according to any one of embodiments 1-33, wherein said calculating a navigation trajectory provides a variable source-to-tumor distance.

Embodiment 35

The method according to any one of embodiments 1-34, wherein said calculating a navigation trajectory provides a trajectory based on consideration of one or more features selected from the group consisting of clearance and mechanical travelling range, acceleration limits to manage patient position stability, total couch movement, gantry traveling distance, and total delivery time.

Embodiment 36

The method according to any one of embodiments 1-35, wherein said calculating a navigation trajectory utilizes the level set method as applied to robotic navigation in constrained spaces.

Embodiment 37

The method according to any one of embodiments 1-36, wherein said calculating a navigation trajectory includes reparamaterizing the planned beams with their associated source-to-tumor distances, and the virtual reality surface (VRS) with respect to the couch translation, rotation, and gantry angle.

Embodiment 38

The method of embodiment 37, wherein said reparamaterizing includes: generating nodes on the VRS generated from the treatment plans to represent the planned beams as $y_q$, $q=1, 2, \ldots, Q$; and defining the collision zone due to mechanical restriction and/or collision geometry as $C \subset \mathfrak{R}^N$ where the goal to seek a path $\gamma(s) \subset \mathfrak{R}^N$, $s \in (0,1)$ that meets the following three requirements: i) γ traverses through $y_q$ for q=1, 2, . . . , Q; ii) γ does not cross C; and iii) γ is optimized.

Embodiment 39

The method of embodiment 38, wherein γ is defined to be minimized.

Embodiment 40

The method of embodiment 38, wherein couch motion and/or speed is limited in one or more directions.

Embodiment 41

The method according to any one of embodiments 38-40, wherein an optimization framework is formalized by quantifying (i) stating that path intersects the beams and (ii) the second that the path does not intersect the collision space (Equation 3):

$$\begin{cases} y_q \in \gamma, \text{ for } q = 1, 2, \ldots, Q. \\ \gamma \cap C = \emptyset \end{cases} \quad (3).$$

Embodiment 42

The method according to any one of embodiments 38-41, wherein a penalty function E considers the variation of the trajectory along each direction (Equation 4):

$$E_i(\gamma) = \lambda_i \int_0^1 |\bar{\gamma}_i(s)| ds, \quad (4)$$

where the penalty function is computed for machine degree of freedom i and interim path $\bar{\gamma}(s)$, $\lambda_i$ is a penalty function that weighs the relative importance of linear accelerator degree of freedom i in the path optimization process.

Embodiment 43

The method of embodiment 42, wherein the optimal path γ is determined by (Equation 5):

$$\text{minimize} \sum_i \lambda_i \int_0^1 |\bar{\gamma}_i(s)| ds, \quad (5).$$

$$\text{s.t.} \begin{cases} y_q \in \bar{\gamma}, \text{ for } q = 1, 2, \ldots, Q. \\ \bar{\gamma} \cap C = \emptyset \end{cases}$$

Embodiment 44

The method of embodiment 43, wherein $\lambda_i$ is set zero for motions that have no impact on delivery accuracy or efficiency.

Embodiment 45

The method of embodiment 44, wherein $\lambda_i$ is set zero for collimator rotation.

Embodiment 46

The method of embodiment 43, wherein $\lambda_i$ is set above to penalize uncomfortable comfortable motion types Embodiment 47

The method of embodiment 46, wherein said motion type is couch rotation.

Embodiment 48

The method according to any one of embodiments 1-47, wherein said providing a set of radiotherapy beam orientations, and/or said selecting a subset of beams; and/or said calculating a navigation trajectory is performed on a local computer.

Embodiment 49

The method according to any one of embodiments 1-47, wherein said providing a set of radiotherapy beam orientations, and/or said selecting a subset of beams; and/or said calculating a navigation trajectory is performed on a local server or on a remote server.

Embodiment 50

The method according to any one of embodiments 1-49, wherein said writing instruction files includes writing one or more instruction files to a tangible medium selected from the group consisting of a magnetic medium, an optical medium, a PAL chip, and a static RAM chip.

Embodiment 51

The method of embodiment 50, wherein said writing instruction files includes writing one or more instruction files to a CD, a flash drive, a DVD, and a hard drive.

Embodiment 52

The method according to any one of embodiments 1-51, wherein said instruction files contain a treatment plan including one or more of the following: machine gantry and couch positions, multileaf collimator positions, beam intensities, imager positions at a given time or plan delivery point.

Embodiment 53

The method according to any one of embodiments 1-52, wherein said radiotherapy device produces electron or photon beams.

Embodiment 54

The method according to any one of embodiments 1-52, wherein said radiotherapy device produces electron, neutron, proton, x-ray, or gamma radiation.

Embodiment 55

The method according to any one of embodiments 1-54, wherein said radiotherapy device includes a linear accelerator (linac).

Embodiment 56

A radiation treatment planning system for preparing treatment planning information for carrying out radiation treatment, said radiation treatment planning system including: an input unit with which an operator inputs at least a prescription dose and a treatment volume; an arithmetic unit that receives a 3D map of the patient surface and the treatment machine, where said arithmetic unit prepares treatment planning information by determining irradiation conditions in such a manner as to bring a dose distribution calculated based on the result of the input from the input unit; and a display unit that displays the treatment planning information; wherein the arithmetic unit determines treatment beams, apertures and calculates machine and table paths using a method according to any one of embodiments 1-52.

Embodiment 57

The system of embodiment 56, wherein said system further includes a 3D scanning system.

Embodiment 58

The system according to any one of embodiments 56-57, wherein said arithmetic unit is configured to receive a CAT scan from a CT scanner or a patient medical record.

Embodiment 59

The system according to any one of embodiments 56-58, wherein said system is configured to output a treatment plan into a patient medical record.

Embodiment 60

A method of performing a radiotherapy treatment on a subject, said method including: inputting into a radiotherapy device controller an instruction file generated using a method according to any one of embodiments 1-52; and operating said radiotherapy device using the inputted instruction set to deliver a radiation to said subject.

Embodiment 61

The method of embodiment 60, wherein said radiotherapy device includes a linac.

Definitions

The term "subject" and "patient" are used interchangeably to refer to a mammal from which a biological sample is obtained to determine sensitivity to ionizing and/or non-ionizing radiation. Subjects can include humans and non-human mammals (e.g., a non-human primate, canine, equine, feline, porcine, bovine, lagomorph, and the like).

The planning target volume or "PTV" in a radiation treatment refers to the volume of tissue that is to be treated with radiation. The planning target volume (PTV) is created by adding a region of tissue to the clinical target volume or "CTV" that compensates for the errors and uncertainties that occur in treating a patient with radiation.

BRIEF DESCRIPTION OF THE DRAWINGS

FIG. 5, panel B, shows beam delivery sequence (lines) generated by the method described herein. Asterisks denote couch and gantry angle positions required for the treatment beams. Color bar shows source-to-tumor distance-1 meter. FIG. 5, panel C, shows a screen capture of a movie showing the actual delivery of a 4π plan in 10 minutes on a Varian TRUEBEAM® machine synchronized to model animation.

DETAILED DESCRIPTION

Non-coplanar radiotherapy using modern medical linear accelerators has been proposed, tested and implemented by many investigators. The first major problem in non-coplanar treatment is collision. The collision between the gantry, couch and patient has been a persistent problem in external beam radiotherapy, more so in non-coplanar treatments. One way to avoid the risk is a dry run with the patient on the couch and the therapist moves the gantry and couch cautiously to test delivery path. The method obviously consumes precious treatment room time and can result in plan revision if a collision is detected. Therefore, most departments also adopt a policy minimizing non-coplanar beam angles that are collision prone. Since both methods are undesired in automated non-coplanar plans involving a large number of beams, pre-planning collision modeling is generally a prerequisite. In one computerized prediction method (see, e.g., Humm (1994) *Med. Phys.* 21: 1053-1064) a simplified 3D surface of the machine is used and combined with experimental measurements of potential collision points. The patient is modeled as a rectangular box fixed to the couch. This method was later adopted and modified to improve visualization (see, e.g., Humm et al. (1995) *Int. J. Radiat. Oncol. Biol. Phys.* 33: 1101-1108; Tsiakalos et al. (2001)*Med. Phys.* 28: 1359-1363; Chao et al. (2001) *J. Digit. Imaging*, 14: 186-191; Becker (2011) *J. Appl. Clin. Med. Phys.* 12: 3405), incorporate patient specific external contours from the CT (Nioutsikou et al. (2003) *Phys. Med. Biol.* 48: N313-N321) and develop an analytical collision model that is, however, computationally inexpensive (Hua et al. (2004) *Med. Phys.* 31: 2128-2134).

Another approach involved digitizing the surface of individual moveable components on external beam therapy machines using and generating an augmented reality environment for virtual operation and collision detection (see, e.g., Hamza-Lup et al. (2008) *Int. J. Comput. Assist. Radiol. Surg.* 3: 275-281). However even using such methods, the individual patient individual are not easily integrated in the collision model and used to guide beam optimization. Additionally it is believed there has not been research on navigation through the non-coplanar beams, which requires complex choreography between patient couch and gantry. When a large number of non-coplanar beams are needed, manual navigation has typically been inefficient and ultimately impractical.

Figure 1:
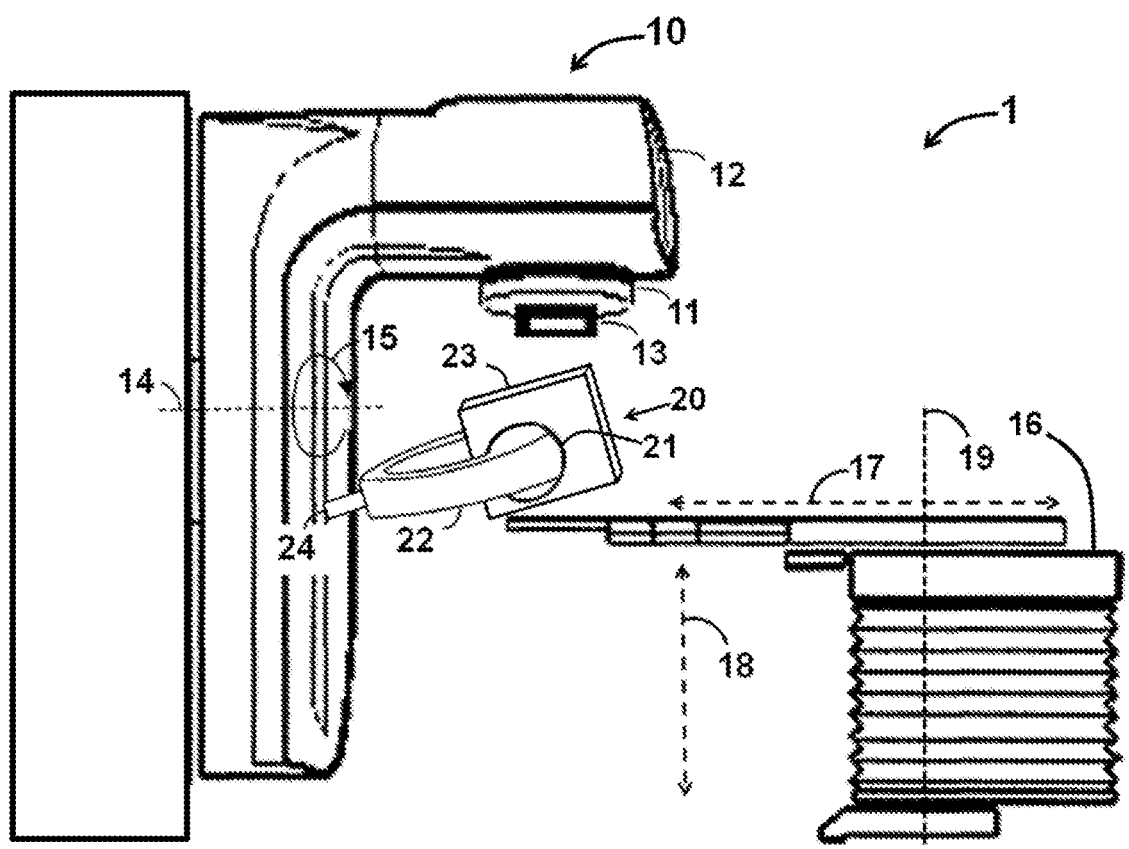
FIG. 1 is an illustrative, but non-limiting schematic view of a radiation treatment system.

The complexity of the problem is illustrated by consideration of an illustrative, but non-limiting, schematic of a treatment room 1 as shown in FIG. 1 (see U.S. Pat. No. 7,130,372). Radiation treatment room 1 includes linear accelerator (linac) 10, optionally an imaging system 20 (comprising, e.g., x-ray tube 21, first support 22, imaging device 23, and second support 24), and patient table 16. The elements of radiation treatment room 01 may be used to deliver treatment radiation to a patient according to a radiation treatment plan. Linac 10 generates and emits the treatment radiation, and is primarily composed of treatment head 11 and gantry 12. Treatment head 11 includes a beam-emitting device (not shown) for emitting a radiation beam that can be used during calibration, verification, and/or treatment. The radiation beam may comprise electron, photon or any other type of radiation. Also typically included within treatment head 11 is a beam-shielding device or collimator (e.g., MLC, not shown) for shaping the beam and for shielding sensitive surfaces from the beam. Optionally accessory tray 13 is mounted on treatment head 11 and may be configured to receive and securely hold attachments used during the course of treatment planning and treatment. These attachments may include reticles, wedges, or the like for further defining field sizes and intensities. Treatment head 11 is fastened to a projection of gantry 12. Gantry 12 is rotatable around gantry axis 14 before, during and after radiation treatment. Although clockwise rotation is indicated by arrow 15, gantry 12 may also or alternatively rotate counter-clockwise according to some embodiments. Rotation of gantry 12 serves to rotate treatment head 11 around axis 14. Patient table 16 is rotatable about axis 19 and translatable along axes 17 and 18 before, during and/or after treatment. During radiation treatment, treatment radiation is delivered from linac 10 to the beam-emitting device of treatment head 11 and is emitted therefrom as a beam. Given the many degrees of freedom offered, inter alia, by rotation of the gantry head, vertical and/or horizontal movements of the table, and varying configurations of a multileaf collimator (MLC), numerous beams at different distances, orientations, shapes and intensities can be provided. Selection and optimization of a manageable subset of such beams, particularly in the utilization of non-coplanar beams, has provided a previously intractable problem.

The method sand devices described herein solve this problem and provide efficient and effective treatment In various embodiments the approach described herein proceeds by:

1) Determining all feasible radiotherapy beam orientations free of collision for a radiotherapy device when used with a particular subject to provide a set of radiotherapy beam orientations;
2) Selecting from the set of all feasible radiotherapy beam orientations a subset of beams that meet treatment goals to be used in treatment of the subject to provide a selected beam set;
3) Calculating a trajectory for the radiotherapy device to delivery said subset of beams to said subject where said trajectory is free of collision; and
4) Generating and writing instruction files to a tangible medium that can be executed by the radiotherapy device (see, e.g., FIG. 1).

More particularly, in the approach described herein, the subject (patient) surface is measured (e.g., using a 3D optical camera) and then integrated into a model of the treatment machine (e.g., the couch and gantry model) which is used to calculate a beam geometry solution space that guides the beam orientation optimization. Modeling the solution space has two advantages. First, the beams selected by the optimization algorithm are deliverable by the particular machine to that particular subject. Second, the methods can automatically expand the solution space to a non-isocentric surface that maximally utilizes the non-coplanar solution space for superior radiation dosimetry.

It is believed that there has not previously been a method, other than manual trial and error, to determine the order of beams and the path to navigate (the radiation machine and/or patient couch) from one beam of the selected treatment set to another. This posed a significant problem in treatments utilizing a large number of non-coplanar beams. For the first time a mathematical solution is presented herein that automatically determines the beam order and efficient path (machine/couch path) connecting these beams. The method significantly reduces treatment time, improves radiation dosimetry and safety, and reduces patient discomfort and undesired intrafractional motion.

More particularly, in various embodiments, the patient surface is digitized, e.g., using a 3D optical camera (Artec MH) and fit onto a model (e.g., a CAD model) of the treatment machine. An exhaustive search of all couch and gantry combinations is performed to determine the minimal distances between the radiation source and the patient. A cocoon is generated from the search and a beam orientation optimization is performed on the surface to determine the beam angles. A level set method as described herein is used to calculate the shortest path traversing the beams. The path is optimized to avoid collision and, optionally, to reduce travel time.

The method can be used in all external beam radiotherapy treatments. The methods and device described herein invention solve practical limitations associated with non-coplanar radiotherapy so the dosimetric gains can be realized without major modification to current practice and increased cost to either patients, manufacturers or the hospitals.

1) Determining all Feasible Radiotherapy Beam Orientations Free of Collision.

A) Virtual Reality Surface (VRS) Generation.

The surface of the subject/patient is mapped, using a scanner to generate a three dimensional model. Three-dimensional scanning can be accomplished using a variety of technologies that include inter alia, contact scanners that probe the subject through physical contact e.g. a CMM (coordinate measuring machine)) and non-contact active scanners.

Non-contact active scanners emit some kind of radiation or light and detect its reflection or radiation passing through object in order to probe an object or environment. Possible types of emissions used include light, ultrasound or x-ray. Such active scanners typically utilize either time-of-flight measurements or triangulation measurements.

Typical time-of-flight scanners (e.g., Microsoft Kinect2) utilize laser light to probe the subject. At the heart of this type of scanner is a time-of-flight laser range finder. The laser range finder finds the distance of a surface by timing the round-trip time of a pulse of light. A laser is used to emit a pulse of light and the amount of time before the reflected light is seen by a detector is measured. Since the speed of light c is known, the round-trip time determines the travel distance of the light, which is twice the distance between the scanner and the surface. If t is the round-trip time, then distance is equal to ct/2 and the accuracy of a time-of-flight 3D laser scanner depends on the precision of the time measurement. The laser range finder typically only detects the distance of one point in its direction of view. Thus, the scanner scans its entire field of view one point at a time by changing the range finder's direction of view to scan different points. The view direction of the laser range finder can be changed either by rotating the range finder itself, or by using a system of rotating mirrors. The latter method is commonly used because mirrors are much lighter and can thus be rotated much faster and with greater accuracy. Typical time-of-flight 3D laser scanners can measure the distance of 10,000~100,000 points every second. Numerous time-of-flight 3D laser scanners are commercially available (see, e.g., Microsoft KINECT2®, FARO FOCUS$^{3D}$®, NEXTENGINE®, and the like).

Triangulation based 3D laser scanners are also active scanners that can use laser light to probe the environment. With respect to time-of-flight 3D laser scanner the triangulation laser shines a laser on the subject and exploits a camera to look for the location of the laser dot. Depending on how far away the laser strikes a surface, the laser dot appears at different places in the camera's field of view. This technique is called triangulation because the laser dot, the camera and the laser emitter form a triangle. The length of one side of the triangle, e.g., the distance between the camera and the laser emitter is known. The angle of the laser emitter corner is also known. The angle of the camera corner can be determined by detecting the location of the laser dot in the camera's field of view. These three pieces of information fully determine the shape and size of the triangle and give the location of the laser dot corner of the triangle. In most cases a laser stripe, instead of a single laser dot, is swept across the object to speed up the acquisition process.

Structured light scanners also use trigonometric triangulation, but instead of looking at laser light, these systems project a series of linear patterns onto an object. Then, by examining the edges of each line in the pattern, they calculate the distance from the scanner to the object's surface. Essentially, instead of the camera seeing a laser line, it sees the edge of the projected pattern, and calculates the distance similarly. Various triangulation-based 3D laser scanners are commercially available (see, e.g., Microsoft Kinect1®, David Laserscanner SLS-2®, REAL3D™ scanner, 3D Underworld Open Source scanner, Artec EVA™, and the like).

Other suitable scanning technologies include laser phase-shift systems. Laser phase-shift systems are another type of time-of-flight 3D scanner technology, and conceptually work similarly to pulse-based systems. However, in addition to pulsing the laser, these systems also modulate the power of the laser beam, and the scanner compares the phase of the laser being sent out and then returned to the sensor.

Still other scanning technologies include conoscope holographic scanners. These scanners measure distances by using the polarization properties of a converging light cone that reflects from an object. An anisotropic crystal is used to split a light a ray that into two components that share the same path but have orthogonal polarizations. The crystal's anisotropic structure forces each of the polarized light rays to propagate at a different velocity, thus creating a phase difference between them. This phase difference enables the formation of an interference pattern that varies with the distance from the object under measurement. In classical holography, a hologram is created by recording an interference pattern formed between an object beam and a reference beam using a coherent light source. The two beams propagate at the same velocity (same refractive index), but follow different geometric paths. This means that when overlapped, the phase difference between the two beams depends only on the geometric path difference. This phase difference is responsible for the creation of a measurable interference pattern that can later be used to reconstruct the original light field. In conoscopic holography, however, a light beam that traverses an optically anisotropic crystal is split into two beams that share the same geometric path but have orthogonal polarization modes. The refractive indices of these two beams generally differ from each other. Therefore, after the two beams exit the crystal an interference pattern is generated. The features of this pattern depend on the distance from the light's source. Since both beams propagate through the same geometric path, conoscopic holography is highly stable in comparison to interferometry-based measurement techniques. Moreover, it is also possible to perform measurements using incoherent light.

In one illustrative, but non-limiting embodiment, the subject (patient) 3D surface is acquired (mapped) at the time of computerized tomography (CT)-simulation using a 3D surface imaging camera array. One illustrative, but non-limiting array consisted of 3 MicroSoft Kinect2 Cameras using the time-of-fly technology. Cameras can be mounted on the CT room ceiling above the CT couch. The cameras can provide a combined view of the patient anterior and lateral surfaces. To increase the field of view in the superior/inferior direction and limit occlusions, the couch can be longitudinally translated during the optical scanning procedure, providing a 3D optical equivalent to a topogram. In various embodiments, 3D measurements accuracy is about 10 mm or better, or about 5 mm or better, or about 1 mm or better with such a measurement geometry and scan times are typically less than about 10 minutes, or less than about 5 minutes or less than about 1 minute. In certain embodiments the 3D measurement corrects for subject involuntary subject movement (e.g., breathing).

B) Fusing the Patient Surface Model onto the Machine Model

Figure 3A:
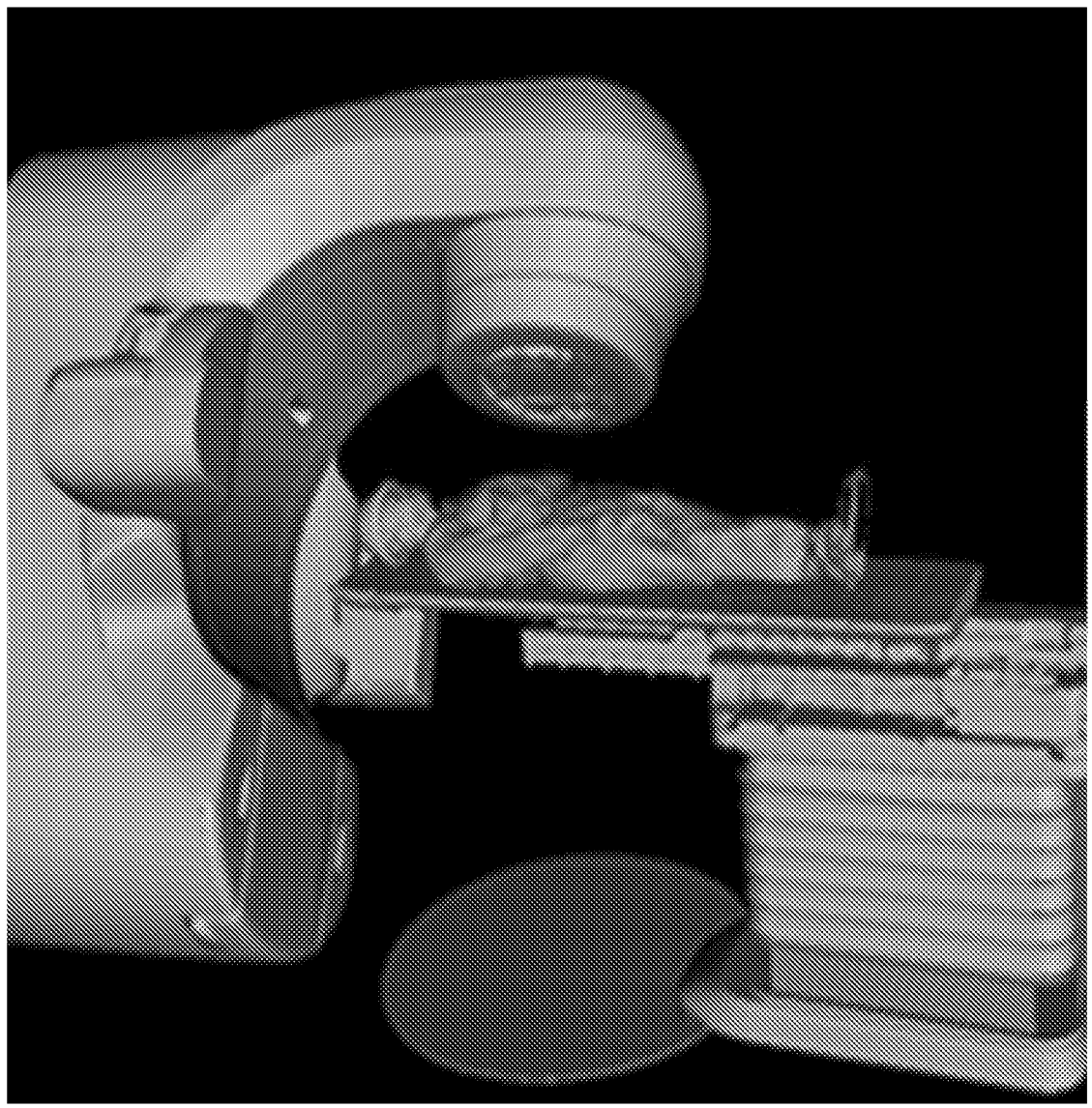
FIG. 3A shows precise modeling of the linac gantry, couch and a human subject using 3D optical cameras.

An example of a scanned human is shown in FIG. 3A. An accurate model of the treatment device can be generated, e.g., using a 3D scanner. In certain instances, an accurate treatment machine model can be provided by the manufacturer. The CAD model represented in FIG. 3A, was based on a CAD model of the linac and couch provided by the vendor and cross-validated using 3D camera measurements. The patient model and device model are fused according to the tumor location, using methods known to those of skill in the art.

C) Constructing the Virtual Treatment Space.

Figure 3B:
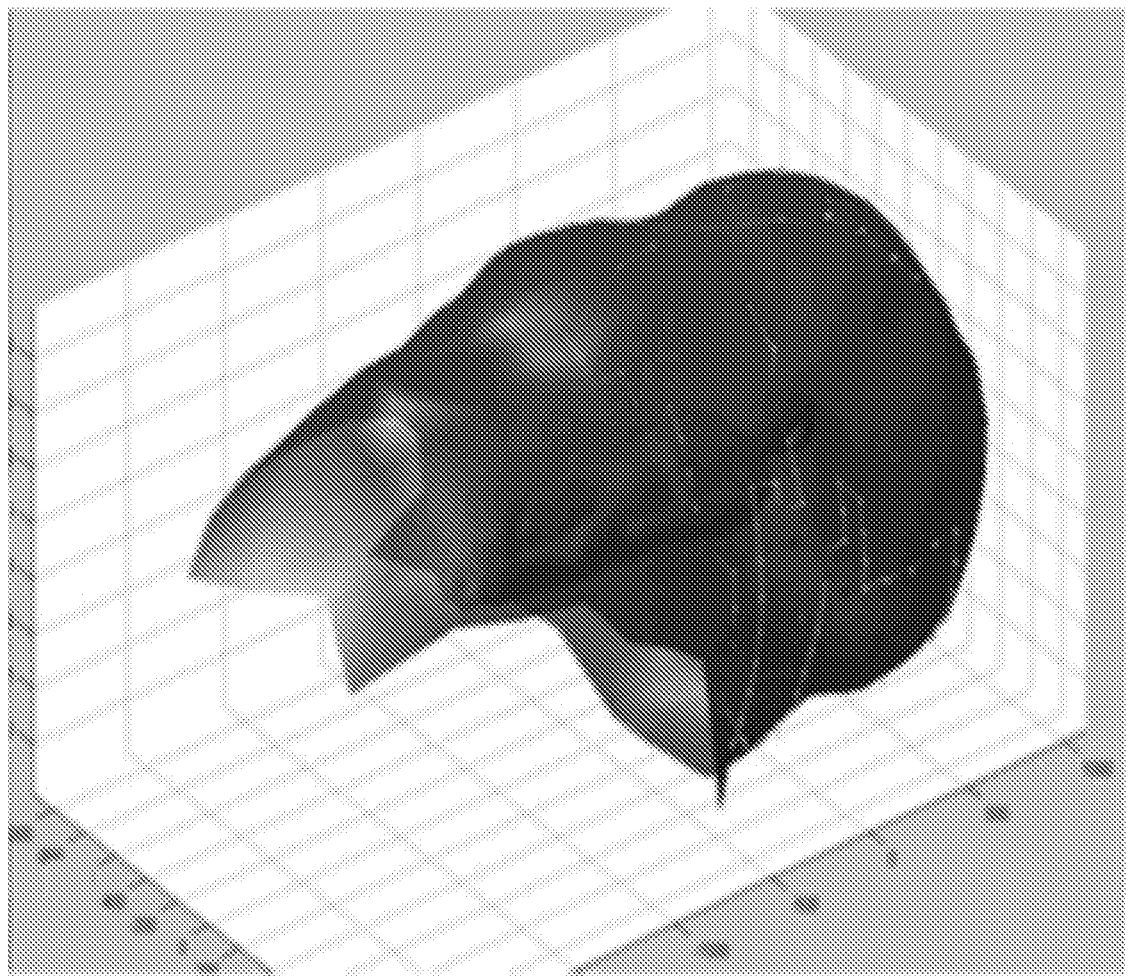
FIG. 3B shows a virtual reality surface (VRS) for a left sided lung tumor. Red dots denote beam orientations and lines are optimized paths as described herein.

FIG. 3B shows an example of a virtual reality surface (VRS) that was generated. In this instance, the VRS employs both variable source-to-tumor distances and a 4 cm added safety margin, termed the collision gap buffer (e.g., to accommodate uncertainties due to patient setup variations, and system modeling, including isocenter accuracies, couch and gantry positioning accuracies, and camera measurement accuracy). It will be appreciated, however, that it is possible to generate a VRS using fixed source-to-tumor distances and/or other added safety margins (collision gap buffers). In certain instances the added safety margin, can be about 0 cm, or about 1 cm, or about 2 cm, or about 3 cm, or about 5 cm, or about 6 cm, or about 7 cm, or about 8 cm, or about 9 cm, or about 10 cm.

D) Determining Beam Angles Free from Collision.

Beam angles that could not be utilized because the couch could not be moved far enough to get out of the way of the gantry, or the gantry would collide with the pedestal, are excluded from the VRS. In this illustrative, but non-limiting example, approximately 75% of the 4π solid angle remains available.

Figure 3C:
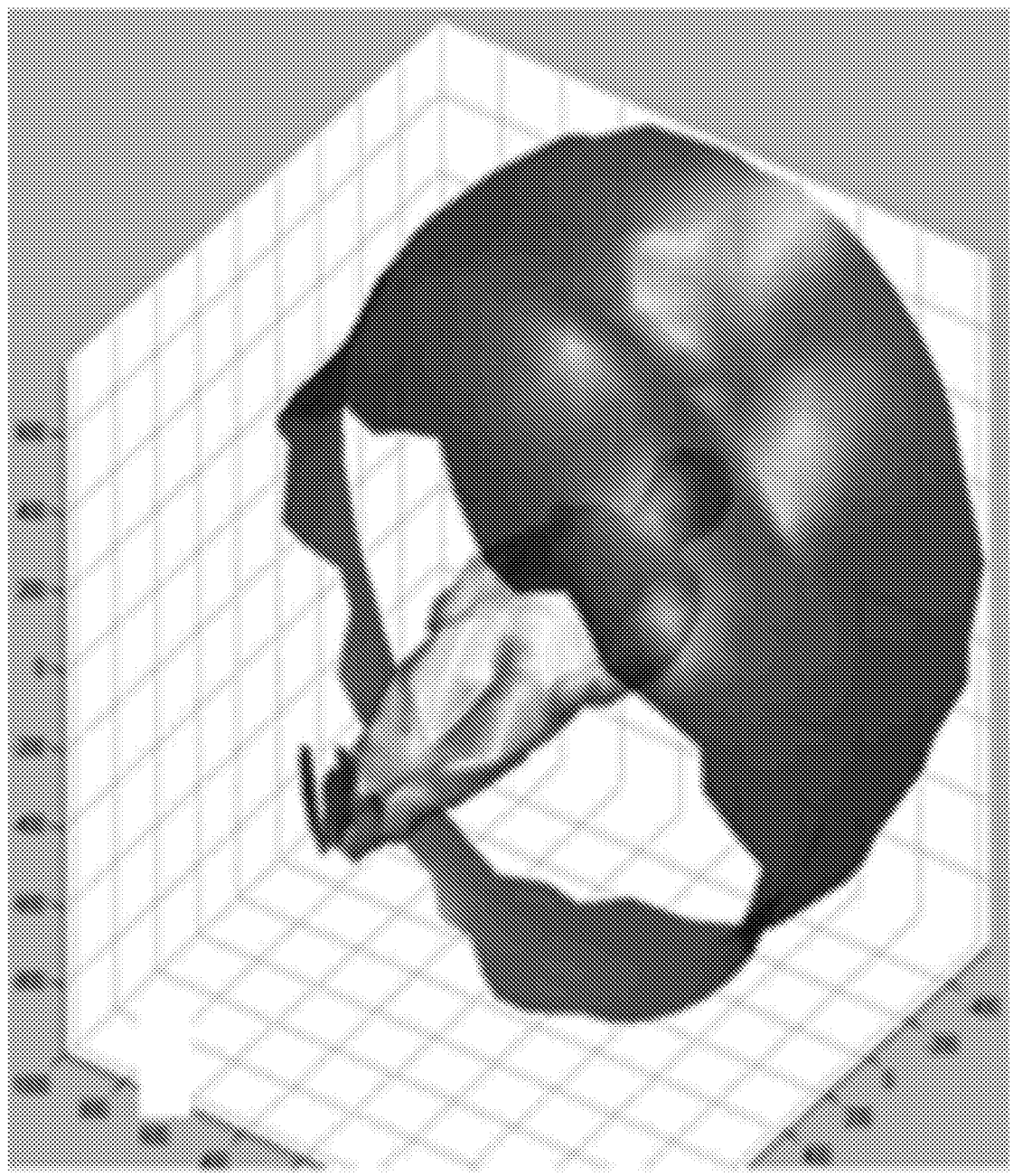
FIG. 3C shows VRS with source-to-tumor distances>100 cm eliminated.

FIG. 3C shows the remaining VRS if an isocentric geometry is employed (VRSi). VRSi is much more constraining than the proposed VRS non-isocentric calculation method for sites outside the cranium and upper head-and-neck. The collision gap buffer are computed using estimated geometric surface measurement uncertainties, patient setup variations, and system modeling, including isocenter accuracies, couch and gantry positioning accuracies and camera measurement accuracy.

2) Selecting from all Feasible Radiotherapy Beam Orientations a Subset of Beams that Meet Treatment Goals.

In various embodiments the treatment plan optimization process selects the most effective beams from all possible beam directions. The angular resolution of the treatment plan can vary from about 1° up to about 10°, or from about 2° up to about 8°, or from about 2° up to about 6°. In certain instances the angular resolution is about 1°, or about 2°, or about 3°, or about 4°, or about 5°, or about 6°, or about 7°, or about 8°, or about 9°, or about 10°.

In the example presented herein, an angular resolution of ~6° was selected which results in 1,170 uniformly distributed beams, termed the beam candidate pool. The algorithm presented herein handles finer beam angle resolution without significantly increasing computational time if meaningful gains are obtained. Patient specific VRSs are obtained and used as described above. Each beam is subdivided into individually calculated beamlets with square cross-sectional lengths corresponding to the multileaf collimator (MLC) leaf width (e.g., 0.5 cm at 100 cm SAD). The dose per fluence is calculated and stored in a database for use during optimization.

A Direct Aperture Optimization (DAO) algorithm is employed for intensity modulation and leaf sequencing that is also based on the idea of column generation and pricing. DAO combines fluence map optimization and leaf sequencing into a single step. It can easily take MLC deliverability constraints (such as interdigitation constraints) into account, as well as dosimetric effects such as transmission and the tongue-and-groove effect and efficiency measures such as beam-on-time.

In one illustrative, but non-limiting, approach, $D_{bk}$ denotes the dose delivered to a volume from aperture a∈$K_b$ in beam b∈B and F(z) the objective function associated with dose distribution z. The optimization problem is then formulated as follows (Equation 1):

$$\text{minimize } F(z) \quad (1)$$

$$\text{s.t.} \begin{cases} \vec{z} = \sum_{b \in B} \sum_{k \in K_b} D_{bk} \, x_{bk}, x_{bk}, \geq 0, k \in K', b \in B \\ x_{bk} = 0, b \in B \backslash B', k \in K' \\ \vec{z} \leq \vec{q} \end{cases}$$

where $K_b$ is the set of deliverable apertures at angle b, B' represents selected beam orientation sets, $\vec{z}$ is the 3D dose distribution, $\vec{q}$ is the 3D dose constraint. Instead of directly solving the large combinatorial model presented above, which would be computationally intractable, a column generation algorithm is used to determine the contents of B' while explicitly taking into account the treatment plan quality. The optimization starts from an empty solution set and for each iteration, beams from the remainder of the candidate beam pool B\B' are individually added to the selected beam set, and the direct aperture optimization problem is subsequently solved. The beam that contributes most to the plan optimization objective function is kept and all other beams are returned to the candidate beam pool. The iterative process continues until the desired number of beams is reached or the objective function plateaued.

To select a new beam, solving the aperture optimization problem with all potential beam candidates and choosing one beam that had the lowest objective function value would have been possible, but the computation time would have been clinically impractical. Instead, the benefit of adding a beam is predicted rather than explicitly computed. The price, i.e., the instantaneous change in the objective value of the optimal solution per unit of the constraint of solving the direct aperture optimization model with selected B' beams is used to predict the value of the new beam. This is known as the Karush-Kuhn-Tucker (KKT)-conditions for optimality. The beam orientation and aperture optimization problem is performed interleaved using CPLEX (Academic Research Edition 12.2). As a baseline, the objective function F(z) is defined based on a linear approximation of equivalent uniform dose (EUD) (see, e.g., Thieke et al. (2002) *Acta Oncologica* 41:158-161) (Equation 2):

$$\begin{cases} F(\vec{z}) = \sum_m \alpha_m G_m(\vec{z}) \, m \in r, s, r_{50}, V_{d_1 Gy}, V_{d_2 Gy}, \ldots V_{d_n Gy}, \alpha_m \geq 0 & (2) \\ Gr(\vec{z}) = \text{mean}(\max(\text{prescription dose} - \vec{z}, 0)) \cdot \text{ for } PTV \, r \\ Gs(\vec{z}) = h_s \, \text{mean}(\vec{z}) + (1 - h_s)\max(\vec{z}) \text{ for } OAR \, s \, h_s \leq 1 \\ Gr_{50}(\vec{z}) = h_{r_{50}} \text{mean}(\max(\vec{z} - 0.5 * \text{prescription dose}, 0)) \\ \qquad \text{for ring structures} \\ G_{V_{d_1 Gy}}(\vec{z}) = \text{mean}(\max(\vec{z} - d_1, 0)) \\ \qquad \text{for an } OAR \text{ such as the lung or heart} \\ G_{V_{d_2 Gy}}(\vec{z}) = \text{mean}(\max(\vec{z} - d_2, 0)) \\ \qquad \ldots \\ G_{V_{d_n Gy}}(\vec{z}) = \text{mean}(\max(\vec{z} - d_n, 0)) \end{cases}$$

where $G_s$, $G_r$, $G_{r_{50}}$, $G_{V_{d_1 Gy}}$, $G_{V_{d_2 Gy}}$ and $G_{V_{d_3 Gy}}$ are objective functions for organs-at-risk (OARs), PTVs, dose gradient as defined by the ratio between the 50% isodose volume and PTV, and the volume of a specific organ receiving greater than $d_1, d_2, \ldots d_n$ doses. $h_s$ is used to adjust the relative weighting of average and maximum dose for serial or parallel organs. $\alpha_m \geq 0$ for OARs, $\alpha_m \leq 0$ for PTV, $h_s \leq 1$, $h_r \leq 1$, respectively. The weights among multi objectives $\alpha_m$'s are fine-tuned to reach individual planning objectives. A shell-shaped structure is added as isotropic expansion of PTV to apply the dose gradient constraint. The assignment of a voxel that that lie within multiple OARs is given to the OAR with greatest optimization priority, which is manually determined.

The number of beams is determined based on the incremental gains in dose conformality ($R_{50}$), which decreases as the number of optimized non-coplanar angles increases. Since there is not a clear plateau, we use a minimal number of beams to reach the optimization goal. Based on our preliminary study, the goal can be reached for all patients using fewer than 30 beams.

Because of the intractable problem size if using an unconstrained number of initial apertures, we limit the initial set of apertures per beam, denoted by $\hat{K}_b \in K_b$. At each iteration, we solve a restricted version of Equation (1) using only the apertures within $\hat{K}_b$. Given the corresponding solution, an optimization subproblem is solved that either (i) identifies one or more promising apertures that improve the current solution when added to $\hat{K}$ or (ii) concludes that no such aperture exists and therefore the current solution is optimal.

Figure 4:
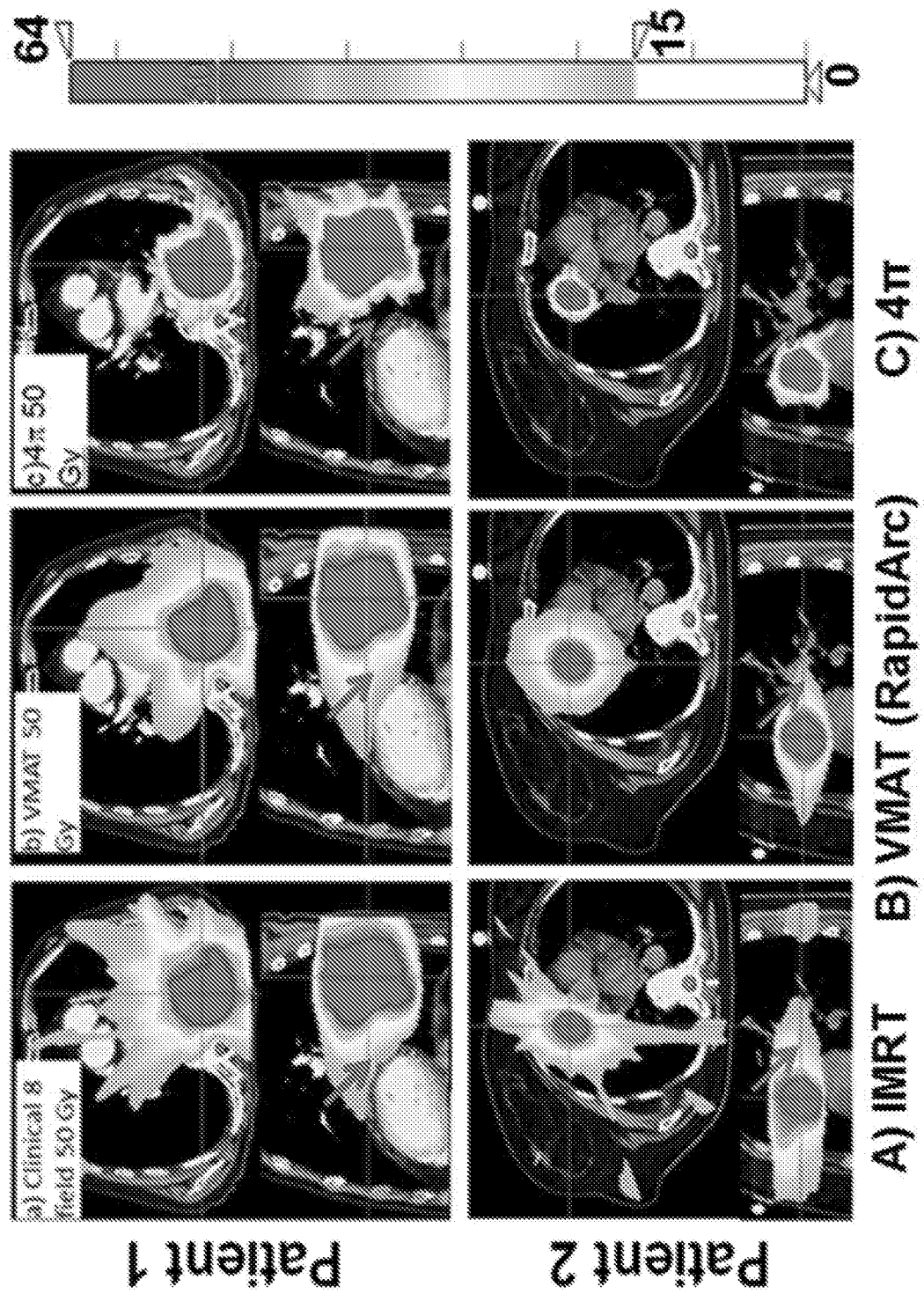
FIG. 4, panels A-C, illustrate dose (Gy) of 3 different planning scenarios. Panel A: clinical 8 field IMRT; Panel B: VMAT plan; Panel C: 30-field 4π plan, for 2 representative patients shown in 2 orthogonal planes. Patient 1 had a large (6.3 cm) tumor and patient 2 had a small tumor abutting the heart. All prescriptions covered 95% of the PTV. The color map low-dose limit was set to 15 Gy, slightly lower than the RTOG 0813 constraints on trachea and ipsilateral bronchus. Arrows point to the location where 4π significantly reduces central organ high doses.
Figure 5:
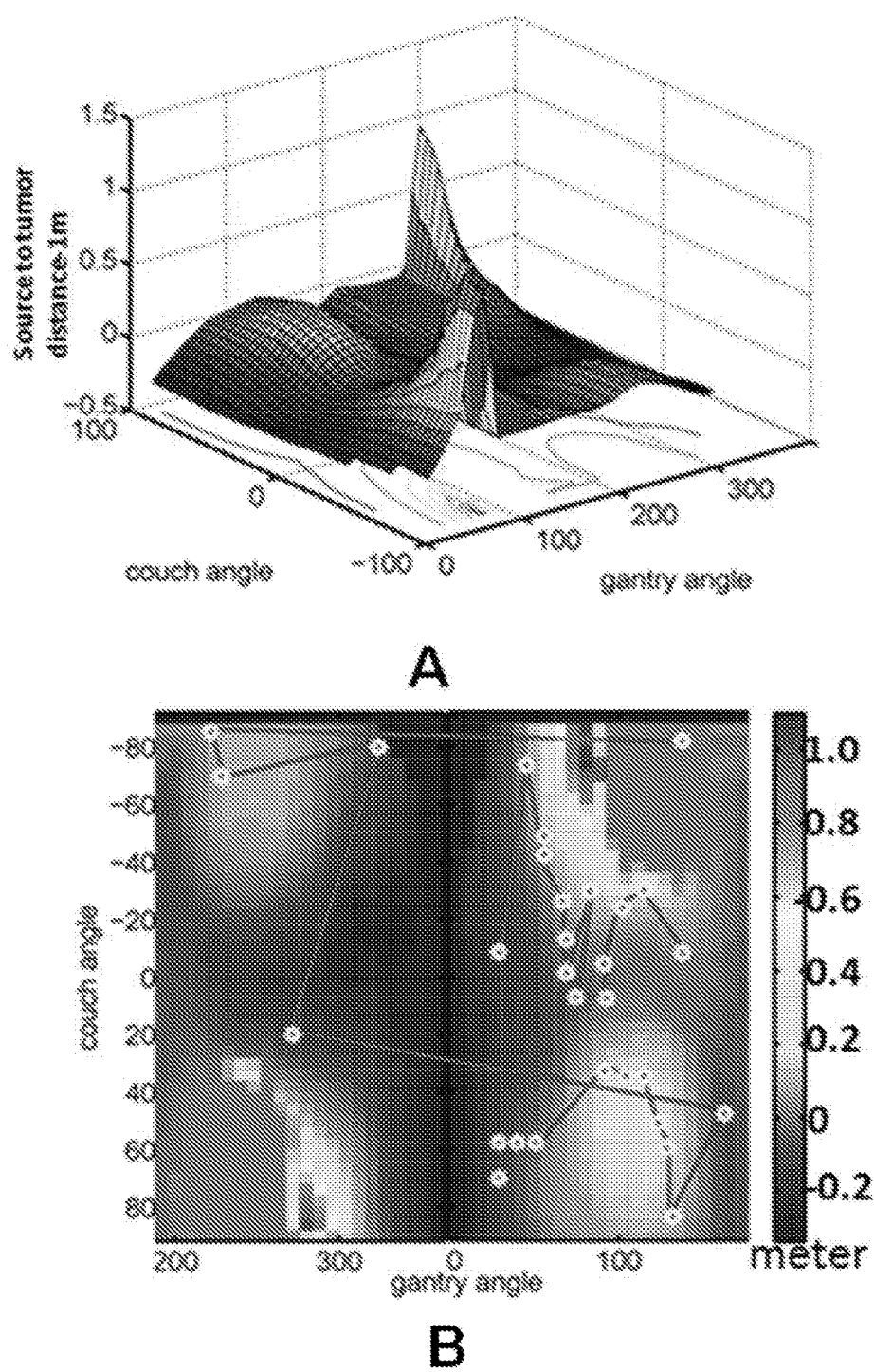
FIG. 5, panel A, shows a 2D surface mesh rendering of the source-to-tumor distance for mathematical formulation of FIG. 3B.
Figure 6:
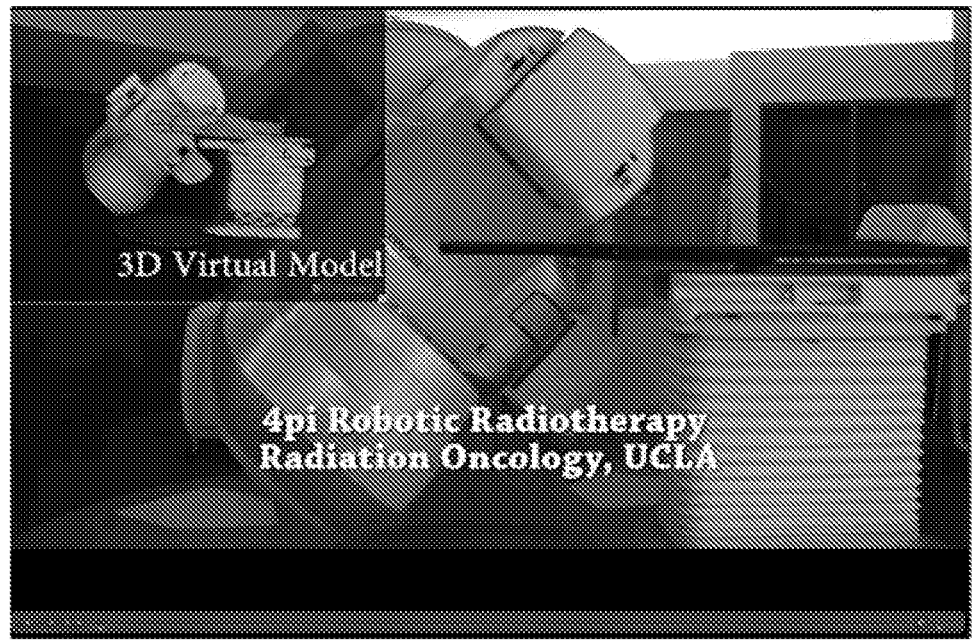
FIG. 6, panels A-H, illustrates screen captures from a video of a radiotherapy machine (Varian TRUEBEAM®) and couch as they move through orientations determined using the methods described herein. The video shows the actual delivery of a 4π plan in 10 minutes.
Figure 6:

FIG. 4, panels A-C, shows the planning results of two lung cancer patients in comparison to their clinical plans. We found that in comparison to 8 field IMRT and VMAT plans utilizing two full arcs, the two non-$4\pi$ plans (FIG. 4, panels A and B) were clinically equivalent to each other but the $4\pi$ plans provided significantly steeper dose gradients (FIG. 4, panel C), reducing R50 by an average of 54%. Additionally, the equivalent uniform dose (EUD) of heart, esophagus, trachea, bronchus and spinal cord were reduced by 44%, 74%, 40%, 42%, and 51% ($p \leq 0.001$), respectively. Lung $V_{20}$, $V_{10}$, and $V_5$ were reduced by 64%, 53% and 32% ($p \leq 0.001$), respectively. These large dosimetric improvements would have enabled a dose escalation for all of the patients from the clinically delivered 50 Gy to a minimum of 68 Gy (range 68 Gy-105 Gy) without increasing organ at risk (OAR) doses relative to the clinical treatment plans.

3) Calculating a Machine Trajectory for Treatment (Optimal Machine Navigation.

In certain embodiments, of the methods described herein treatment positions are optimized such that the gantry is often positioned close to the patient, couch, or pedestal, so the path between beams require continuous and explicit collision avoidance. This distinguishes the current problem from conventional node navigation schemes (e.g., in CYBERKNIFE® system) where line segment between pairs of nodes are designed to be clear of collision and the physical distance defines the association cost for the corresponding travelling salesman problem. The variable source-to-tumor distance gives rise to a continuous path optimization problem on the VRS that is generally neither Euclidean nor globally convex. To this end, an optimization problem is solved with a cost objective that incorporates feasibility considerations such as clearance and mechanical travelling range, acceleration limits to manage patient position stability, as well as efficiency considerations including total couch movement, gantry traveling distance, and total delivery time. In various embodiments the level set method as applied to robotic navigation in constrained spaces is utilized.

In order to optimize a smooth transition path that traverses all beams, we the planned beams are reparameterized with their associated source-to-tumor distances, and the virtual reality surface (VRS) with respect to the couch translation, rotation, and gantry angle. Nodes on the VRS generated from the treatment plans can be used to represent the planned beams as $y_q$, $q=1, 2, \ldots, Q$ and define the collision zone due to mechanical restriction and/or collision geometry as $C \subset \Re^N$. The goal is to seek a path $\gamma(s) \subset \Re^N$, $s \in (0,1)$ that meets the following three requirements:

i) $\gamma$ traverses through $y_q$ for $q=1, 2, \ldots, Q$;
ii) $\gamma$ does not cross C; and
iii) $\gamma$ is optimized.

Optimizing $\gamma$ may be defined by the user by minimizing $\gamma$, or by minimizing specific motions such as couch vertical due to maximum speed constraints or to assure patient comfort and stability.

To meet the three path requirements, an optimization framework is formalized by quantifying the requirements as either constraints or penalties. The first two requirements are constraints, the first stating that path intersects the beams and the second that the path does not intersect the collision space (Equation 3):

$$\begin{cases} y_q \in \gamma, \text{ for } q = 1, 2, \ldots, Q. \\ \gamma \cap C = \emptyset \end{cases} \quad (3)$$

To optimize the path length, we penalty function E is developed that considers the variation of the trajectory along each direction (Equation 4):

$$E_i(\gamma) = \lambda_i \int_0^1 |\bar{\gamma}_i(s)| ds, \quad (4)$$

where the penalty function is computed for machine degree of freedom i and interim path $\gamma_i(s)$. $\lambda_i$ is a penalty function that weighs the relative importance of linear accelerator degree of freedom i in the path optimization process. $E_i$ penalizes the total amount of variation along degree of freedom i, discouraging long or cursive paths. Given the previous definition, the optimal path $\gamma$ is determined by (Equation 5):

$$\text{minimize} \sum_i \lambda_i \int_0^1 |\bar{\gamma}_i(s)| ds, \quad (5)$$

$$\text{s.t.} \begin{cases} y_q \in \bar{\gamma}, \text{ for } q = 1, 2, \ldots, Q. \\ \bar{\gamma} \cap C = \emptyset \end{cases}$$

This formulation allows us to set $\lambda_i$ to zero for motions that have no impact on delivery accuracy or efficiency, as may be in the case of collimator rotation. On the other hand, $\lambda_i$ is can be set to be large to penalize less comfortable motion types, such as couch rotation.

4) Generating and Writing Instruction Files to a Tangible Medium.

In various embodiments the treatment plan instruction file comprising, inter alia, a treatment beam set, a trajectory for the treatment device including, for example, gantry orientations, table orientations, trajectories of gantry and table between such orientations, and optionally apertures, is written to a computer readable medium. In certain embodiments the treatment plan instruction file contains one or more of the following: machine gantry and couch positions, multileaf collimator positions, beam intensities, and imager positions at a given time or plan delivery point. In typical embodiments, the file includes inter alia all delivery points describing machine and/or couch travel path(s) and timing (e.g., timing of travel paths and/or beam times) that are needed for a complete treatment.

Illustrative, but non-limiting computer readable media, include, but are not limited to magnetic media (e.g., hard, or "floppy" drives, optical media (e.g., CD, DVD), solid state drives, programmable array logic (PAL) chip(s), static RAM, and the like. In certain embodiments, the output is to local media and/or to remote media (e.g., a server, a cloud server, an internet site, and the like).

In certain embodiments, particularly where the device is a linac, the data file may be an xml file, although other file formats are contemplated.

In various embodiments, the methods described herein are performed using a treatment planning system.

Figure 7:
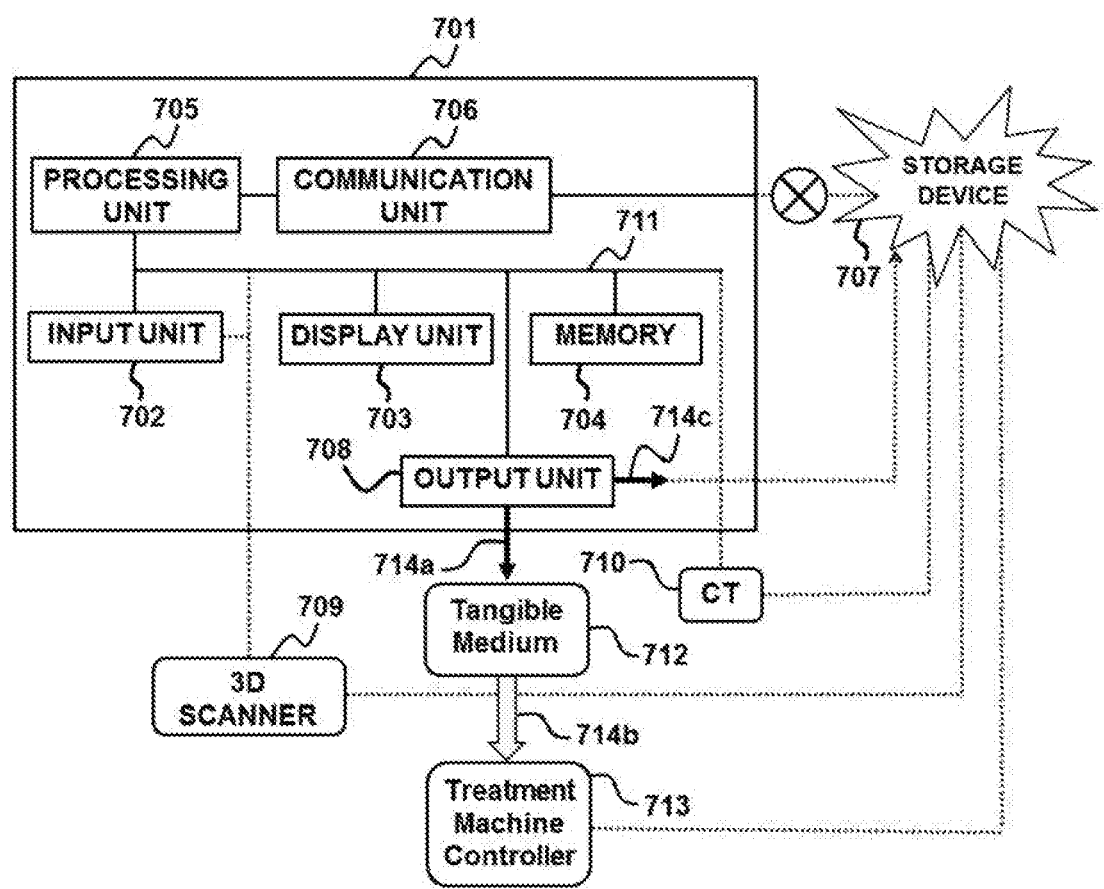
FIG. 7 schematically illustrates components that may comprise one embodiment of a treatment planning system.

FIG. 7 schematically illustrates components that may comprises one non-limiting embodiment of a treatment planning system. As illustrated in FIG. 7, the treatment planning system 701 includes an input component (e.g., unit) 702, a display component (e.g., unit) 703, a memory 704, a computer processor (e.g., a specialized or a general purpose computer processing unit) (CPU), 705, and a communication component 706. The CPU unit 705 is connected to the input component 702, display component 703, memory (storage unit) 704, and, optionally, communication unit 706. In certain embodiments the treatment planning system 701 is connected to a storage device 707 (e.g., a hard drive or solid state drive), or data server directly e.g., via a dedicated line), or via a network. Where the storage device 707 (e.g., data server) is on a network, the network can be a local network or a wide area network, e.g., the data server can be accessed through the internet or other wide area network). In embodiments, where the storage device is local, it can be a drive connected directly to bus 711. In certain embodiments, the storage device/data server stores patient medical records. In certain embodiments, communication unit 706 of the treatment planning system 701 is connected to the storage device 707 via the network and exchanges data with the storage device.

In certain embodiments the patient to be treated has had computed tomography images obtained at treatment planning time or beforehand using a CT apparatus 710. Treatment planning information and CT data/images acquired by the CT apparatus 710 (CT data) is stored on the storage device 707. The CT data is typically three-dimensional data made of CT values recorded per small region called a voxel. The treatment planning system 701 can use the CT data in preparing the treatment plan.

In certain embodiments the patient to be treated has had 3D surface maps generated from the patient in treatment position which can be obtained at treatment planning time or beforehand using a 3D scanner 709. Similarly 3D models of the treatment device can be scanned in or can be provided from a source e.g., from the treatment device manufacturer). In various embodiments 3D patient and/or machine surface maps can be stored on the storage device 707 for use in treatment planning using the methods described herein.

Figure 2:
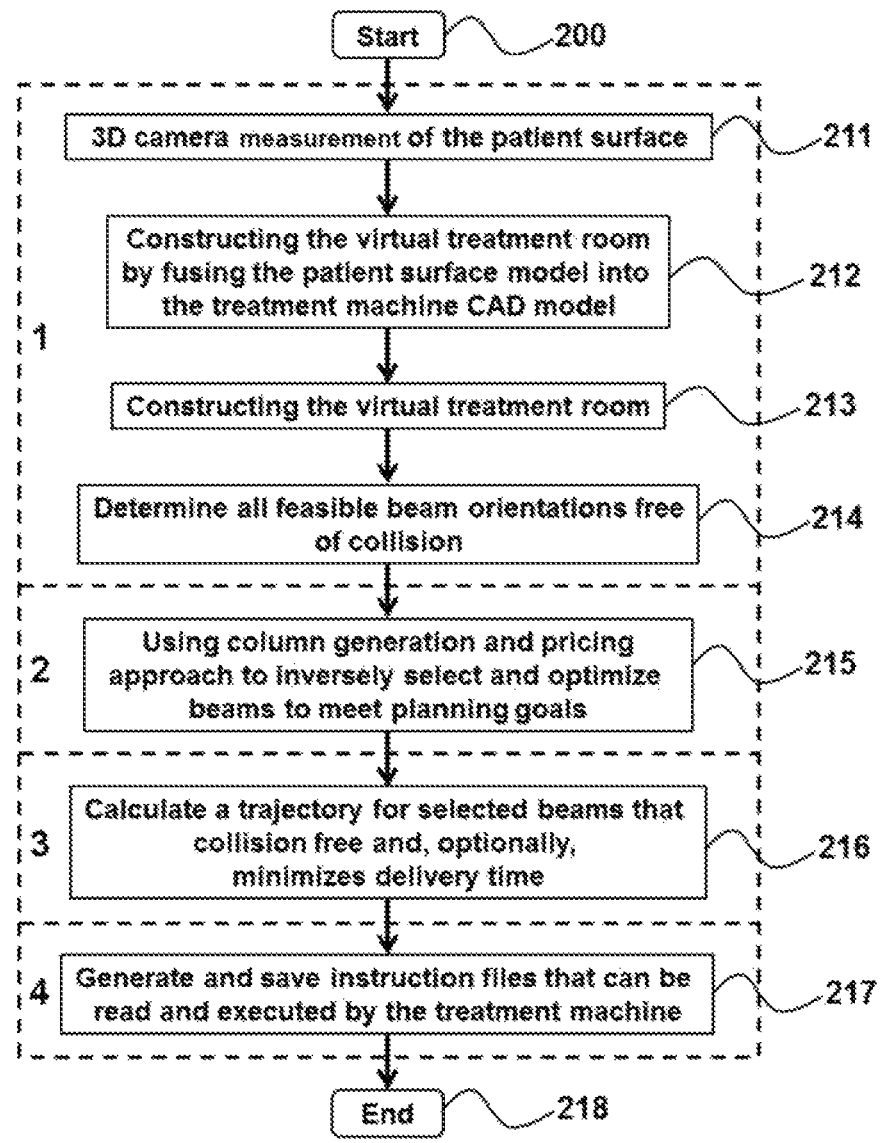
FIG. 2 is a flow diagram of process steps according to some embodiments.

When a healthcare professional (e.g., physician) acting as the operator inputs patient information (e.g., a patient ID or identifying information) through the input unit 702, the treatment planning system 701 starts to prepare treatment planning information about the patient corresponding to the patient ID (see, e.g., process in FIG. 2, step 200). The input unit 702 outputs the input patient ID to the processing unit 705. Based on the patient ID, the processing unit 705 retrieves the 3D map of the patient surface (step 211), e.g., directly from 3D scanner 709, or from storage device 707, or from local input, e.g., from a flash drive, and merges this surface with the machine model (step 212) to generate a virtual treatment room (step 213). Based on treatment parameters (e.g., dose, planning treatment volume an location, etc.) input by the user and/or stored on storage device 707, for example along with CT information stored from CT 710, and/or from storage device 707, all feasible beam orientations free of collision (FIG. 2, step 214) are determined, e.g., by processor 705. Processor 705 then selects and optimizes beams to meet treatment planning goals (step 215) and, in certain embodiments, this process may utilizes further user input provided through input unit 702 and/or from data storage device 707. After determination of an optimized beam set, a trajectory is calculate for the selected beams that is collision free and, optionally minimizes delivery time (step 216). The treatment information (e.g., beams (e.g., orientations and apertures, delivery time(s), machine and couch positions, and trajectories is formatted into one or more instruction file(s) (e.g., 714a. 7141, 714c) that can be read and executed by the treatment machine controller 713 and saved to tangible media (e.g., optical media, magnetic media, solid-state media, etc.) (step 217).

It will be appreciated that the treatment planning system shown in FIG. 7 is simply illustrative and non-limiting. Using the teachings provided herein numerous configurations will be available to one of skill in the art. For example, in certain embodiments, the processing unit 705, the communication unit 706, bus 711, input unit 702, display unit 703, memory 704, storage device 707 and output unit 708 can all be provided in a single self-contained treatment planning machine. In certain embodiments, the storage device 707 can be remote, e.g., on a local or remote server (e.g., a patient record server). In certain embodiments, the user interface can be provided locally, while the computational components are remote, e.g., on a local or remote server (e.g., an internet site). In certain embodiments, the processing unit can comprise a plurality of processors that are present locally or that are distributed. In certain embodiments the scanner 709 can provide scan data directly to treatment planning system 701 and/or can provide data to storage device 707. Similarly in certain embodiments, CT 710 can provide data directly to treatment planning system 701 and/or to storage device 707. Similarly, in various embodiments output unit 708 can output instruction files directly to tangible medium 712, and/or to storage device 707. Similarly, in certain embodiments, tangible medium 712 can provide instruction file 714b to be read directly by treatment machine controller 713 and/or instruction file 714c can be provided to treatment machine controller 713 directly from storage device 707.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of generating a radiotherapy plan for treating a subject on a radiotherapy device, the method comprising:
    generating a virtual treatment surface based on the radiotherapy device and the subject;
    determining, based on the virtual treatment surface, a set of radiotherapy beams that avoid collision for the radiotherapy device and subject;
    selecting, from the set of radiotherapy beams, a subset of radiotherapy beams that meet treatment goals for the subject;
    calculating a navigation trajectory that delivers the subset of radiotherapy beams free of collision;

writing, to a tangible medium, instructions executable by the radiotherapy device in accordance with the subset of radiotherapy beams and navigation trajectory.

2. The method of claim 1, wherein the method further comprises generating a subject surface model using a map of the three-dimensional (3D) surface of the subject.

3. The method of claim 2, wherein the method further comprises scanning the subject using a non-contact active scanner, a time of flight active scanner, a triangulation based 3D laser scanner, a structured light 3D scanner, one or more cameras positioned about the subject, or a combination thereof, to generate the map.

4. The method of claim 2, wherein the method further comprises generating the map using a 3D measurement accuracy that is better than about 5 mm, or better than about 4 mm, or better than about 3 mm, or better than about 2 mm, or better than about 1 mm.

5. The method of claim 2, wherein generating the virtual treatment surface comprises fusing the subject surface model with a model of the radiotherapy device.

6. The method of claim 1, wherein the method further comprises selecting the subset of radiotherapy beams consistent with an isocentric geometry or a non-isocentric geometry.

7. The method of claim 1, wherein the method further comprises generating the radiotherapy plan by applying a Direct Aperture Optimization (DAO) algorithm to determine intensity modulation and leaf sequencing.

8. The method of claim 7, wherein the method further comprises combining fluence map optimization and leaf sequencing into a single step.

9. The method of claim 1 wherein the method further comprises formulating an optimization problem as:

$$\text{minimize } F(z)$$
$$\text{s.t.} \begin{cases} \vec{z} = \sum_{b \in B} \sum_{k \in K_b} D_{bk} \, x_{bk}, x_{bk} \geq 0, k \in K', b \in B \\ x_{bk} = 0, b \in B \backslash B', k \in K' \\ \vec{z} \leq \vec{q} \end{cases}$$

wherein $F(z)$ an objective function associated with a 3D dose distribution $\vec{z}$, $D_{bk}$ is a dose to a volume from aperture $a \in K_k$ for beam $b \in B$, $K_b$ is a set of deliverable apertures for beam angle b, B' are selected beam orientation sets, and $\vec{q}$ is a 3D dose constraint.

10. The method of claim 9, wherein the method further comprises applying a column generation algorithm to determine B'.

11. The method of claim 10, wherein the method further comprises performing an iterative process by:
setting an empty solution set for B';
for each iteration, adding beams from a candidate beam pool B\B' to a selected beam set;
selecting a beam that contributes most to the objective function and returning all other beams to the candidate beam pool; and
continuing the iterative process until a desired number of beams is obtained or the objective function reaches a plateau.

12. The method of claim 11, wherein selecting the beam comprises computing a direct aperture optimization problem or predicting a benefit of adding the beam.

13. The method of claim 9, wherein the objective function $F(z)$ is defined based on a linear approximation of equivalent uniform dose (EUD) and at least objective functions for at least one of organs at risk and planning target volumes.

14. The method of claim 1, wherein the method further comprises calculating the navigation trajectory that minimizes delivery time for the subset of radiotherapy beams.

15. The method of claim 1, wherein the method further comprises utilizing an optimization framework to calculate the navigation trajectory, the optimization framework comprising a cost objective that considers at least one of clearance, mechanical travelling range, acceleration limits, total couch movement, gantry traveling distance, and total delivery time.

16. The method of claim 1, wherein the method further comprises utilizing a level set method to calculate the navigation trajectory.

17. The method of claim 16, wherein the method further comprises reparametrizing the subset of radiotherapy beams and virtual reality surface with respect to couch translation, couch angle, and gantry angle.

18. The method of claim 17, wherein the method further comprises generating nodes on the reparametrized virtual reality surface using the subset of radiotherapy beams, and defining a collision zone based on at least one of collision geometry and mechanical restriction corresponding to the radiotherapy device.

19. The method of claim 18, wherein the navigation trajectory corresponds to a path that traverses the nodes and does not cross the collision zone.

20. The method of claim 19, wherein the path is optimized according to a penalty function that considers degrees of freedom of the radiotherapy device.

21. The method of claim 1, wherein the instruction includes a radiotherapy plan instruction file comprising machine gantry positions, couch positions, multileaf collimator positions, beam intensities, and imager positions.

22. A treatment planning system for generating a radiotherapy plan for treating a subject on a radiotherapy device, the treatment planning system comprising:
an input unit configured to receive input from an operator;
a processing unit configured to:
determine, based on a virtual treatment surface, a set of radiotherapy beams that avoid collision for the radiotherapy device and subject;
select from the set of radiotherapy beams a subset of radiotherapy beams that meet treatment goals;
calculate a navigation trajectory that delivers the subset of radiotherapy beams;
generate instructions executable by a radiotherapy device in accordance with the subset of radiotherapy beams and navigation trajectory,
an output unit configured provide the instructions.

23. The system of claim 22, wherein the processing unit is further configured to generate the virtual treatment surface using a model of the radiotherapy device and a subject surface model generated using a map of the three-dimensional (3D) surface of the subject.

24. The system of claim 22, wherein the processing unit is further configured to select the subset of radiotherapy beams consistent with an isocentric geometry or a non-isocentric geometry.

25. The system of claim 22, wherein the processing united is further configured to utilize an optimization framework to calculate the navigation trajectory, the optimization framework comprising a cost objective that considers at least one of clearance, mechanical travelling range, acceleration limits, total couch movement, gantry traveling distance, and total delivery time.

26. The system of claim 22, wherein the system is further configured to generate the radiotherapy plan based on the subset of radiotherapy beams.

27. The system of claim 26, wherein the system further comprises a display unit configured to display information associated with the radiotherapy plan.

* * * * *

UNITED STATES PATENT AND TRADEMARK OFFICE
CERTIFICATE OF CORRECTION

PATENT NO. : 10,549,116 B2  
APPLICATION NO. : 15/555669  
DATED : February 4, 2020  
INVENTOR(S) : Ke Sheng et al.

Page 1 of 2

It is certified that error appears in the above-identified patent and that said Letters Patent is hereby corrected as shown below:

In the Specification

Column 4, Eq. (1), Line 1, " $\vec{z} = \sum_{b \in B} \sum_{k \in K_b} D_{bk} x_{bk}, x_{bk}, \geq 0, k \in K', b \in B$ " should be -- $\vec{z} = \sum_{b \in B} \sum_{k \in K_b} D_{bk} x_{bk}, x_{bk}, \geq 0, k \in K', b \in B$ --.

Column 5, Eq. (2), Line 1, " $F(\vec{z}) = \sum_m \alpha_m G_m(\vec{z}) m \in r, s, r_{50}, V_{d_1Gy}, V_{d_2Gy}, \ldots V_{d_nGy}, \alpha_m \geq 0$ " should be -- $F(\vec{z}) = \sum_m \alpha_m G_m(\vec{z}) m \in r, s, r_{50}, V_{d_1Gy}, V_{d_2Gy}, \ldots V_{d_nGy}, \alpha_m \geq 0$ --.

Column 7, Eq. (5), Line 1, "minimize $\sum_i \lambda_i \int_0^1 |\overline{\gamma}_i(s)| ds,$ " should be --minimize $\sum_i \lambda_i \int_0^1 |\overline{\gamma}_i(s)| ds,$ --.

Column 15, Eq. (1), Line 1, " $\vec{z} = \sum_{b \in B} \sum_{k \in K_b} D_{bk} x_{bk}, x_{bk}, \geq 0, k \in K', b \in B$ " should be -- $\vec{z} = \sum_{b \in B} \sum_{k \in K_b} D_{bk} x_{bk}, x_{bk}, \geq 0, k \in K', b \in B$ --.

Column 16, Eq. (2), Line 1, " $F(\vec{z}) = \sum_m \alpha_m G_m(\vec{z}) m \in r, s, r_{50}, V_{d_1Gy}, V_{d_2Gy}, \ldots V_{d_nGy}, \alpha_m \geq 0$ " should be -- $F(\vec{z}) = \sum_m \alpha_m G_m(\vec{z}) m \in r, s, r_{50}, V_{d_1Gy}, V_{d_2Gy}, \ldots V_{d_nGy}, \alpha_m \geq 0$ --.

Signed and Sealed this  
Twenty-sixth Day of May, 2020

Andrei Iancu  
*Director of the United States Patent and Trademark Office*

CERTIFICATE OF CORRECTION (continued)
U.S. Pat. No. 10,549,116 B2

Column 18, Eq. (5), Line 1, "minimize $\sum_i \lambda_i \int_0^1 |\bar{\gamma}_i(s)| ds,$" should be --minimize $\sum_i \lambda_i \int_0^1 |\bar{\gamma}_i(s)| ds,$ --.

In the Claims

Column 21, Claim 9, Line 40, "$\vec{z} = \sum_{b \in B} \sum_{k \in K_b} D_{bk} x_{bk}, x_{bk}, \geq 0, k \in K', b \in B$" should be --$\vec{z} = \sum_{b \in B} \sum_{k \in K_b} D_{bk} x_{bk}, x_{bk}, \geq 0, k \in K', b \in B$ --.